United States Patent
Rathjen

(10) Patent No.: US 11,439,535 B2
(45) Date of Patent: Sep. 13, 2022

(54) OPHTHALMIC DEVICE FOR TREATING AN EYE

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 0 days.

(21) Appl. No.: 16/851,521

(22) Filed: Apr. 17, 2020

(65) Prior Publication Data

US 2020/0330268 A1    Oct. 22, 2020

(30) Foreign Application Priority Data

Apr. 17, 2019    (EP) ..................................... 19169910

(51) Int. Cl.
*A61F 9/008*    (2006.01)

(52) U.S. Cl.
CPC .... *A61F 9/008* (2013.01); *A61F 2009/00851* (2013.01); *A61F 2009/00872* (2013.01); *A61F 2009/00878* (2013.01)

(58) Field of Classification Search
CPC ............ A61F 9/008; A61F 2009/00851; A61F 2009/00872; A61F 2009/00878; A61F 2009/00846; A61F 9/00825
See application file for complete search history.

(56) References Cited

U.S. PATENT DOCUMENTS

| 10,098,783 | B2 * | 10/2018 | Chernyak | ............... A61F 9/008 |
| 2002/0183772 | A1 * | 12/2002 | Lieberman | .......... A61F 9/00819 606/166 |
| 2010/0256965 | A1 * | 10/2010 | Rathjen | ............... A61F 9/00831 703/11 |
| 2011/0301582 | A1 * | 12/2011 | Farrer | ................. A61F 9/00827 606/5 |

(Continued)

FOREIGN PATENT DOCUMENTS

| DE | 102014225635 A1 | 6/2016 |
| DE | 102015013237 A1 | 4/2017 |

(Continued)

OTHER PUBLICATIONS

Oct. 1, 20190—(EP) Search Report—App 19169910.7.

*Primary Examiner* — Brian T Gedeon
*Assistant Examiner* — Joshua Andrew Schum-Houck
(74) *Attorney, Agent, or Firm* — Banner & Witcoff, Ltd.

(57) ABSTRACT

An ophthalmic device for treating an eye includes a laser source, a scanner system and an application head with a focusing optic and a patient interface for docking the application head onto the eye. Moreover, the ophthalmic device includes a measurement system for optically capturing eye structures when the application head is docked to the eye and a circuit which is configured to determine reference structures of the eye, which are arranged in ring-shaped fashion about the center axis of the anterior chamber of the eye, from the captured eye structures and to arrange a defined three-dimensional treatment model with respect to these reference structures in order to process a three-dimensional treatment pattern in accordance with the arranged three-dimensional treatment model in the eye.

14 Claims, 11 Drawing Sheets

(56) References Cited

U.S. PATENT DOCUMENTS

| | | | | |
|---|---|---|---|---|
| 2015/0018674 A1* | 1/2015 | Scott | ................... | A61F 9/00825 |
| | | | | 600/427 |
| 2017/0100282 A1* | 4/2017 | Seiler | ................... | A61B 3/1015 |
| 2019/0000563 A1* | 1/2019 | Schneider | ............... | A61B 34/25 |

FOREIGN PATENT DOCUMENTS

| | | | |
|---|---|---|---|
| EP | 1358839 | A1 | 4/2002 |
| EP | 1430829 | A1 | 6/2004 |
| EP | 2236109 | A1 | 10/2010 |
| EP | 3266427 | | 10/2010 |
| WO | 2014/172621 | A2 | 10/2014 |

* cited by examiner

OPHTHALMIC DEVICE FOR TREATING AN EYE

CROSS-REFERENCE TO RELATED APPLICATION

The present application claims priority to and the benefit of European Patent Application 19169910.7 filed Apr. 17, 2019, which is incorporated by reference herein its entirety.

FIELD OF TECHNOLOGY

The present disclosure relates to an ophthalmic device for treating an eye. The present disclosure relates more particularly to an ophthalmic device for treating an eye by means of a pulsed laser beam in accordance with a three-dimensional treatment model, wherein the ophthalmic device includes an application head with a focusing optic and a patient interface for affixing the application head to the eye.

PRIOR ART

Ophthalmic laser systems that treat the eye tissue, typically the cornea and/or the lens of the eye, by means of a focused pulsed laser beam according to a three-dimensional incision model are used for the refractive correction of an eye, in which the refractive power of the eye is modified. In order to create the three-dimensional incision model during a preparatory planning or examination phase and subsequently apply this during the laser treatment of the eye for the purposes of generating the corresponding three-dimensional incision pattern in the eye to be corrected, the patient must gaze at a fixation target with the relevant eye in order to create a defined alignment of the eye both in relation to the measurement or planning device and, subsequently, in relation to the treating ophthalmic laser system.

A method for measuring the corneal topography and the alignment during surgical treatment of the cornea, within the scope of which the eye of a patient is docked to a patient interface when the patient casts their gaze on a fixation light and the eye is aligned to the axis of the treating laser system is described in US 2015/0018674.

Both measurement data of the eye and reference features are determined when the eye is measured or diagnosed, for example reference marks generated on the eye, such as, e.g., light reflections (in particular Purkinje reflections), which are generated in a plan view of the eye (frontal view) on account of radiating in light using the measurement or planning device, or physiological features of the eye, such as, e.g., arteries in the sclera, the limbus, the iris and the pupil or features of the retina, or dyes applied to the eye. The three-dimensional incision model is defined on the basis of the captured measurement data and with respect to the captured reference features.

EP 2 236 109 describes a planning device comprising a reference generator for defining and storing a geometric reference with respect to a three-dimensional eye model, an incision surface editor for defining and positioning incision surfaces in the three-dimensional eye model and an incision pattern generator for generating three-dimensional incision patterns for tissue cuts to be carried out in the eye by means of femtosecond laser pulses.

The same situation is reproduced during the treating using the treating ophthalmic laser system as during the measurement or diagnosis. That is to say, the patient directs their gaze back on an appropriately arranged fixation target and (preferably same) features are then determined in situ; i.e., under the treating ophthalmic laser system. If the reference features of the eye determined by the measurement data and used for the three-dimensional incision model are brought into correspondence with the corresponding features in situ, during the treatment, a three-dimensional incision pattern can be generated in the eye tissue, said three-dimensional incision pattern corresponding to the three-dimensional incision model in terms of form and size and being positioned in the eye tissue with respect to the reference features.

However, a problem arising in the methods in which the patient aligns their eye on a fixation target in the measurement/planning phase and in the treatment phase is that different or poor alignments of the viewing direction of the eye on the fixation target in the measurement/planning phase and/or in the treatment phase can lead to positioning and alignment errors in the incision pattern to be cut. Moreover, these errors can also be caused by virtue of, for example, the eye not being well-positioned under the laser system and/or a patient interface slipping prior to or during the docking procedure, after which it is no longer affixed. Then, the eye is twisted or tilted with respect to the patient interface, and hence also with respect to the laser system, since the patient interface is arranged in coaxial fashion with the optical axis of the laser system. Furthermore, reference markings may no longer be visible upon contact of the eye with the patient interface, depending on the laser system, since the optical imaging changes.

SUMMARY

It is an aspect of the present disclosure to propose an ophthalmic device for treating an eye, which no longer comprises at least some of the disadvantages of the prior art. In particular, it is an aspect of the present disclosure to propose an ophthalmic device for treating an eye, which device does not mandate a fixation of the viewing alignment on a fixation target during the treatment.

According to the present disclosure, these aspects are achieved by the features of the independent claim. Moreover, further advantageous embodiments emerge from the dependent claims and the description.

An ophthalmic device for treating an eye includes a laser source configured to generate a pulsed laser beam; an application head with a focusing optic and a patient interface, wherein the focusing optic is configured to focus the pulsed laser beam in the eye and wherein the patient interface is configured to affix the application head on the eye; a circuit configured to store a three-dimensional treatment model of a three-dimensional treatment pattern to be processed in the eye; a scanner system configured to direct the pulsed laser beam, in accordance with the three-dimensional treatment model, onto treatment targets of the three-dimensional treatment pattern to be processed in the eye; and a measurement system configured to optically capture structures of the eye when the application head is affixed to the eye. In one embodiment variant, the measurement system is configured to capture three-dimensional eye structures.

In a first aspect of the disclosure, the aforementioned aspects are achieved, in particular, by the present disclosure by virtue of the circuit being configured to determine reference structures of the eye on the basis of the structures optically captured by the measurement system when the application head is affixed to the eye, which reference structures are arranged in substantially ring-shaped fashion about a center axis of the anterior chamber of the eye, and by virtue of the circuit being configured to store a positioning reference point for positioning the three-dimensional treatment model in the eye, to determine, using the reference structures, a positioning reference point that has been displaced when the application head is affixed to the eye, to position the three-dimensional treatment model with respect to the displaced positioning reference point when the application head is affixed to the eye and, when the application head is affixed to the eye, to control the scanner system in such a way that the scanner system directs the pulsed laser beam, in accordance with the three-dimensional treatment model that has been positioned with respect to the displaced positioning reference point, onto the treatment targets of the three-dimensional treatment pattern to be processed in the eye.

In a second aspect of the disclosure, the aforementioned aspects are achieved, in particular, by the present disclosure by virtue of the circuit being configured to determine reference structures of the eye on the basis of the structures optically captured by the measurement system when the application head is affixed to the eye, which reference structures are arranged in substantially ring-shaped fashion about a center axis of the anterior chamber of the eye, and by virtue of the circuit being configured to align the three-dimensional treatment model with respect to the optically captured reference structures and, when the application head is affixed to the eye, to control the scanner system in such a way that the scanner system directs the pulsed laser beam, in accordance with the three-dimensional treatment model that has been aligned with respect to the optically captured reference structures, onto the treatment targets of the three-dimensional treatment pattern to be processed in the eye.

It should be pointed out here that the term "alignment" or "align" should be understood to mean an arrangement and orientation, in terms of direction, of a two-dimensional or three-dimensional object with respect to a spatial reference system. By way of example, if a reference plane and a reference axis, e.g., a center axis, are defined for the captured reference structures, the alignment or the arrangement and orientation, in terms of direction, of the three-dimensional treatment model can be defined by means of tilt and rotation angles with respect to this reference plane and/or this reference axis.

In one embodiment variant of the second aspect of the disclosure, the circuit is configured to store a positioning reference point for positioning the three-dimensional treatment model in the eye, to determine, using the reference structures, a positioning reference point that has been displaced when the application head is affixed to the eye, to position the three-dimensional treatment model with respect to the displaced positioning reference point when the application head is affixed to the eye and, when the application head is affixed to the eye, to control the scanner system in such a way that the scanner system directs the pulsed laser beam, in accordance with the three-dimensional treatment model that has been positioned with respect to the displaced positioning reference point, onto the treatment targets of the three-dimensional treatment pattern to be processed in the eye.

It should be pointed out here that the term "positioning" should be understood to mean an arrangement of an object with respect to a point in a spatial reference system. By way of example, if a positioning reference point for a center point (or any other reference point) of the three-dimensional treatment model is defined for the purposes of positioning the three-dimensional treatment model in the eye, then the treatment model is positioned in the eye with respect to this positioning reference point when the center point of the treatment model (or its other reference point) is arranged on the positioning reference point (however, this does not define a specific alignment of the three-dimensional treatment model).

The embodiments described below are applicable to the first and the second aspect of the disclosure.

In an embodiment, the circuit is configured to determine three-dimensional reference structures of the eye on the basis of the optically captured eye structures.

In an embodiment, the circuit is configured to store the positioning reference point with reference measurement data for positioning the positioning reference point with respect to the reference structures when the application head is not affixed to the eye and to determine the displaced positioning reference point when the application head is affixed to the eye using the reference measurement data and the reference structures determined when the application head is affixed to the eye.

In an embodiment, the reference measurement data include distance specifications from the positioning reference point to at least two opposing points on the reference structures, arranged in substantially ring-shaped fashion, when the application head is not affixed to the eye and the circuit is configured to determine the displaced positioning reference point when the application head is affixed to the eye using the distance specifications with respect to the at least two opposing points on the reference structures determined when the application head is affixed to the eye.

In an embodiment, the distance specifications define path lengths along captured eye structures of the eye from the positioning reference point to the at least two opposing points on the reference structures that are arranged in substantially ring-shaped fashion.

In an embodiment, the distance specifications include path lengths along a neutral axis of the cornea, the corneal front surface and/or the corneal back surface.

In an embodiment, the circuit is configured to determine the displaced positioning reference point when the application head is affixed to the eye using a ratio of the distance specifications contained in the reference measurement data.

In an embodiment, the reference measurement data include a distance specification and a projection point of the positioning reference point with respect to a plane which is defined by reference structures captured when the application head is not affixed to the eye; and the circuit is configured to determine the displaced positioning reference point when the application head is affixed to the eye using the distance specification and the projection point of the positioning reference point with respect to the reference plane when the application head is affixed to the eye.

In an embodiment, the circuit is configured to determine, on the basis of the determined reference structures, a center axis of the anterior chamber defined by the reference structures and to align the three-dimensional treatment model with respect to the center axis of the anterior chamber.

In an embodiment, the circuit is configured to determine a reference plane that extends through the reference structures and to align the three-dimensional treatment model with respect to the reference plane.

In an embodiment, the reference structures include the limbus, the iris, the anterior chamber angle, the scleral spur, Schlemm's canal and/or Schwalbe's line.

In an embodiment, the circuit is configured to receive the three-dimensional treatment model via a communication line from an external planning device.

In an embodiment, the measurement system is configured to optically capture the structures of the eye over a depth range extending in the direction of an optical axis of the focusing optic.

In an embodiment, the measurement system is embodied as an interferometric measurement system and the circuit is configured to control the measurement system in such a way that the measurement system optically captures the structures of the eye when the application head is affixed to the eye and to determine the reference structures from the optically captured structures. Three-dimensional eye structures and reference structures can be determined by means of the interferometric measurement system.

In an embodiment, the measurement system is configured to capture the structures of the eye in one or more cross-sectional images of the eye and the circuit is configured to determine the reference structures of the eye from the one or more cross-sectional images of the eye. Three-dimensional eye structures and reference structures can be determined by way of capturing and using a plurality of cross-sectional images.

In an embodiment, the patient interface includes a contact body that rests on the eye when the application head is affixed to the eye and that deforms the eye. The circuit is configured to transform the three-dimensional treatment model into a deformed three-dimensional treatment model of a deformed three-dimensional treatment pattern to be processed in the eye, to determine, using the reference structures, a positioning reference point that has been displaced when the application head is affixed to the eye and to position the deformed three-dimensional treatment model with respect to the displaced positioning reference point when the application head is affixed to the deformed eye and, when the application head is affixed to the deformed eye, to control the scanner system in such a way that the scanner system directs the pulsed laser beam, in accordance with the deformed three-dimensional treatment model that has been positioned with respect to the displaced positioning reference point, onto the treatment targets of the deformed three-dimensional treatment pattern to be processed in the eye.

BRIEF DESCRIPTION OF THE DRAWINGS

An embodiment of the present disclosure is described below on the basis of an example. The example of the embodiment is illustrated by the following attached figures.

DETAILED DESCRIPTION

Figure 1:
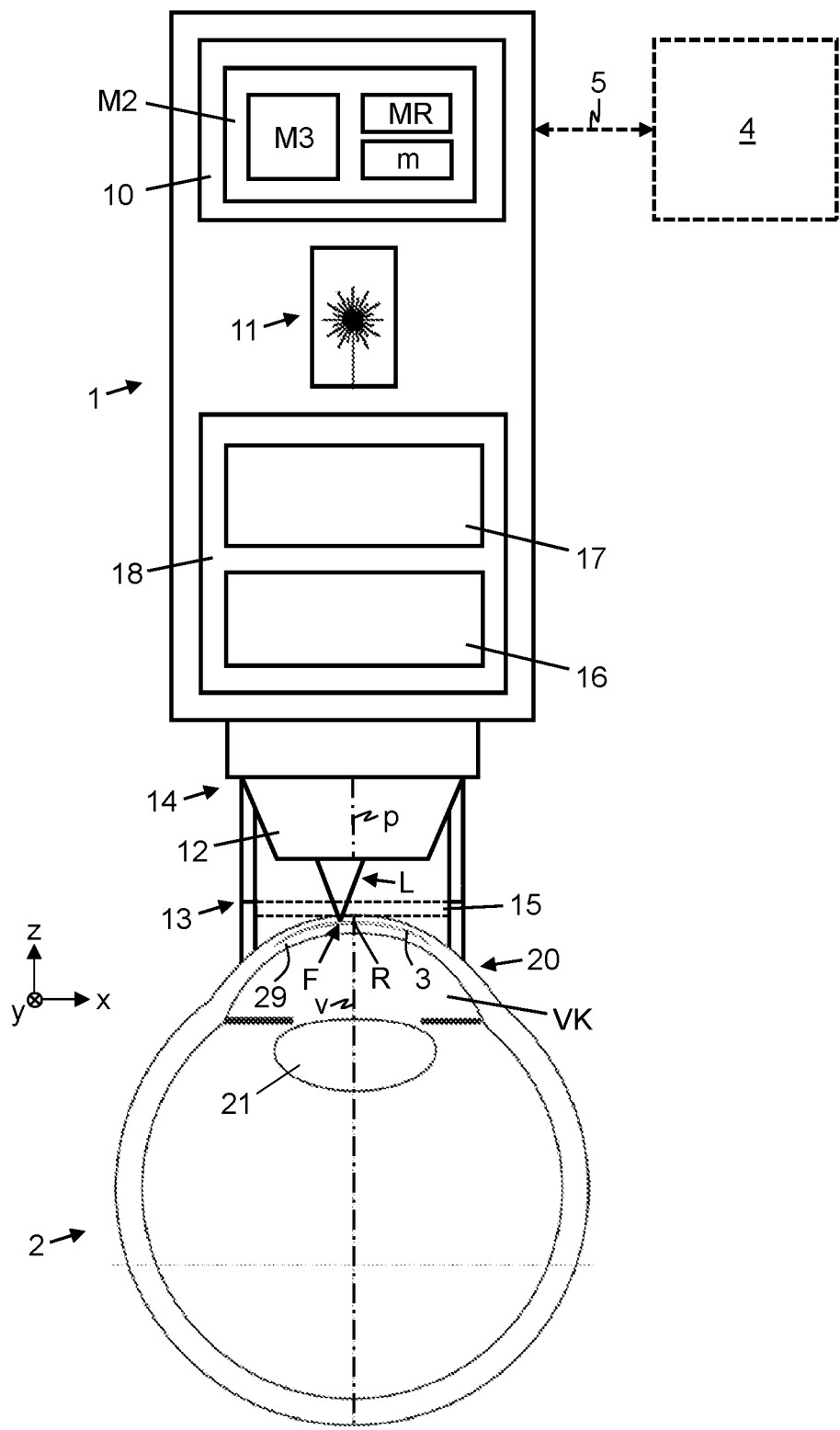
FIG. 1 schematically shows, in a block diagram, an ophthalmic device with a laser source and a focusing optic for treating an eye, affixed to the eye by means of a patient interface.
Figure 2:
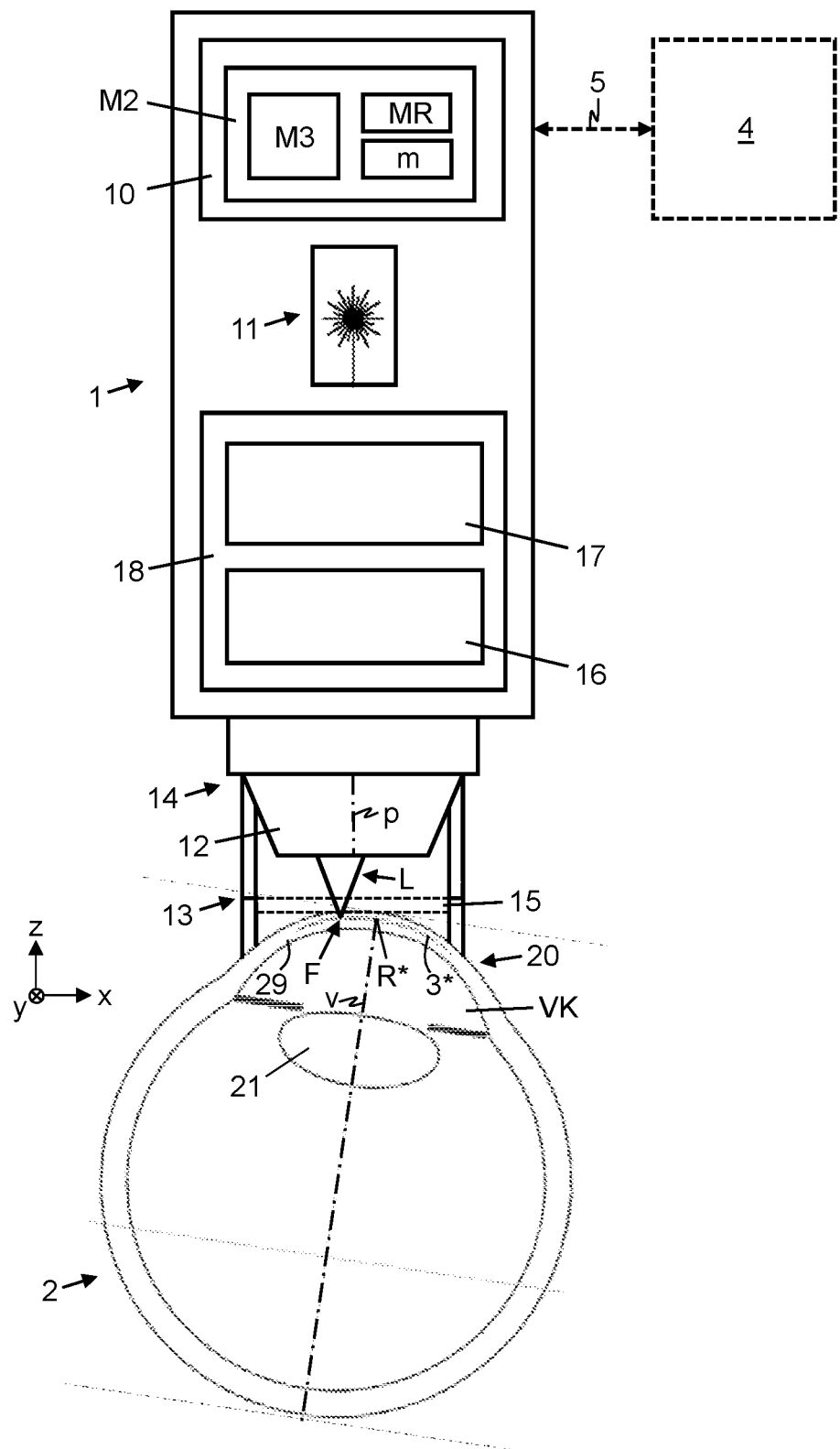
FIG. 2 schematically shows, in a block diagram, an ophthalmic device with a laser source and a focusing optic for treating the eye, affixed in tilted fashion to the eye by means of the patient interface.

In FIGS. 1 and 2, reference sign 1 relates to an ophthalmic device for treating an eye 2 by means of a pulsed laser beam L. The ophthalmic device 1 includes a laser source 11, which is configured to generate the pulsed laser beam L, for example a laser beam L pulsed with femtosecond laser pulses.

As illustrated schematically in FIGS. 1 and 2, the ophthalmic device 1 includes an application head 14 with a focusing optic 12 and a patient interface 13. The patient interface 13 is configured to affix the application head 14 to the eye 2. To this end, the patient interface 13 includes, for example, a suction ring for affixing the application head 14 to the eye 2 by means of negative pressure. In an embodiment, the patient interface 13 is embodied as a liquid-based patient interface 13, in which, in the docked state of the eye 2, an interface chamber is created between the focusing optic 12 and the docked eye 2, said interface chamber being filled with a light-transmitting liquid by way of a supply line. In an embodiment, the patient interface 13 includes an optional contact body 15, which deforms the eye 2 in the docked state, for example applanates said eye or leads to a different predetermined form of the contact body 15, as is illustrated in FIGS. 5, 13, 16 and 18 in exemplary fashion.

The pulsed laser beam L is supplied to the focusing optic 12 from the laser source 11 via an optical transmission system 18. The focusing optic 12 has an optical axis p and includes a lens system with a plurality of optical lenses and is configured to focus the pulsed laser beam L in the eye 2, into eye tissue 20, e.g., into the cornea 29 or into the lens 21 of the eye, or into an implant arranged in the eye, when the application head 14 is docked on the eye 2. By way of example, the laser source 11 and the application head 14 are arranged in separate housings, which are interconnected by way of a rigid or movable carrier arm.

FIG. 1 illustrates the ophthalmic device 1 when it is docked to the eye 2, wherein the optical axis p of the focusing optic 12 is aligned in coaxial fashion with the center axis v of the anterior chamber VK of the docked eye 2.

FIG. 2 illustrates the ophthalmic device 1 when it is docked to the eye 2, with the eye 2 being tilted with respect to the application head 14 such that the center axis v of the anterior chamber VK of the docked eye 2 is aligned in tilted fashion with respect to the optical axis p of the focusing optic 12 (i.e., the optical axis p of the focusing optic 12 and the center axis v of the anterior chamber VK extend neither coaxially nor parallel to one another).

The optical transmission system 18 includes a scanner system 17, which is configured to direct the pulsed laser beam L, in accordance with a three-dimensional (x, y, z) treatment model M3, onto treatment targets F of a three-dimensional treatment pattern 3 to be processed in the eye 2 (targeted positioning of the focus of the pulsed laser beam L on x/y/z-treatment targets F in the eye 2 in accordance with the treatment model M3). Depending on the embodiment or the application mode, and the parameters of the pulsed laser beam L (in particular the laser energy and focal spot dimension thereof) accompanying this, the treatment model M3 defines an incision model M3 of a three-dimensional incision pattern 3 to be cut in the eye tissue 20, in which incision pattern eye tissue is dissolved or removed for cutting or ablating, for example a lenticule, or a treatment model M3 of a three-dimensional treatment pattern 3 to be irradiated into the eye 2, in which the eye tissue 20 or an object in the eye 2, e.g., an implant, is modified, for example in respect of its optical properties such as refractive index and/or light transmissivity, without being dissolved or removed in the process. To this end, the scanner system 17 includes one or more beam-deflecting optical elements, for example controllable movable mirrors (x/y processing direction) and divergence modulators (z processing direction), or controllable lens systems for directing the pulsed laser beam L onto the treatment targets F of the three-dimensional treatment pattern 3. In an embodiment, the scanner system 17 includes a drive system with electric motors for displacing the focusing optic 12 in one or more scanning or processing direction.

Moreover, the ophthalmic device 1 includes a measurement system 16, which is configured to optically capture (in situ) structures of the eye 2 when the eye 2 is docked and to store these in digitized fashion for further analysis purposes.

In an embodiment, the measurement system 16 is configured to capture three-dimensional eye structures when the eye 2 is docked. In an embodiment, the measurement system 16 is configured to capture a three-dimensional (in situ) eye model when the eye 2 is docked. By way of example, the measurement system 16 is embodied as an interferometric measurement system (for optical coherence tomography, OCT), as a triangulating or as a confocal measurement system, and/or includes an optical recording apparatus for capturing cross-sectional images of the eye 2. The interferometric measurement system is configured to optically capture the structures of the eye 2 over a depth range extending in the direction of an optical axis p of the focusing optic 12 and facilitates the capture of three-dimensional eye structures (and reference structures) of the eye 2 for a three-dimensional (in situ) eye model. The interferometric measurement system is coupled into the optical path to the focusing optic 12, for example by way of an optical input coupling element, e.g., a beam splitter cube or an input coupling mirror, into the optical path of the optical transmission system 18. When capturing cross-sectional images, for example by capturing illuminated light cross sections in the eye 2 by means of one or more Scheimpflug-type arranged image sensors, as described in EP 1358839, for example, three-dimensional eye structures or a three-dimensional (in situ) eye model can be captured from a plurality of captured cross-sectional images of illuminated light cross sections, for example as described in EP 1430829.

For the purposes of controlling the ophthalmic device 1, a circuit 10 is provided, which is connected to the laser source 11, the scanner system 17 and the measurement system 16 via control or data lines. By way of example, the circuit 10 comprises ASICs (application-specific integrated circuits), program-code programmed microprocessors and/or other electronic circuitry. As illustrated schematically in FIGS. 1 and 2, the circuit 10 includes data memory for storing a three-dimensional eye model M2 and a three-dimensional treatment model M3 of a three-dimensional treatment pattern 3 to be processed in the eye 2, with a positioning reference point MR and reference measurement data m for positioning the treatment model M3 in the eye 2. By way of example, the circuit 10 is configured to receive the eye model M2, including the (three-dimensional) eye structures described in more detail below, and the three-dimensional treatment model M3 with the positioning data (positioning reference point MR, reference measurement data m) from an external planning device 4 via a communication path 5, e.g., via a LAN or WLAN ((wireless) local area network) connection.

Figure 3:
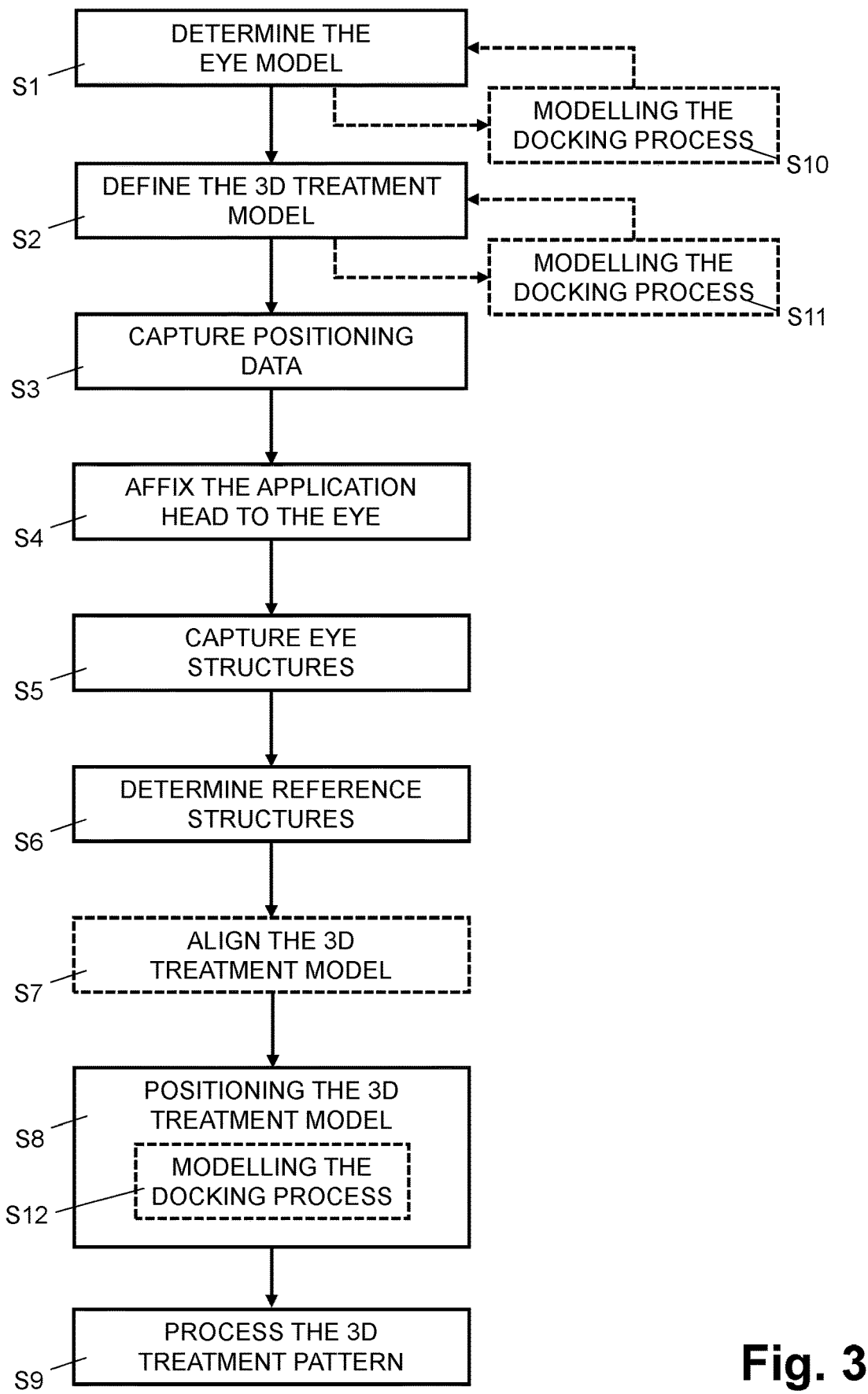
FIG. 3 shows a flowchart that illustrates an exemplary sequence of steps for treating an eye.

A sequence of steps for treating the eye 2 is described below with reference to FIG. 3.

In a preparatory step S1, a three-dimensional eye model M2 of the eye 2 to be treated is captured and stored by means of an external ophthalmic planning device 4. In the treatment, the eye structures of the eye 2 are determined and stored as part of the eye model M2, as explained below. Suitable planning devices 4 are known to a person skilled in the art. The eye model M2 is determined when the eye 2 has a certain alignment, for example by specifying a viewing direction target on which the patient aligns their gaze during the measurement process, or said determination includes a subsequent alignment of the eye model M2 in the case of capture without fixation of the viewing direction. The center axis v of the anterior chamber VK of the eye 2 is aligned in both cases, for example in coaxial fashion with respect to the optical axis of the measurement optical unit or to a vertical reference axis of the planning device 4 (e.g., in the z-direction). The alignment of the eye model M2 following the capture is implemented, for example, by a user by means of suitable software applications in the external planning device 4, e.g., by means of computer-assisted design programs (CAD applications), which are known to a person skilled in the art, or the center axis v of the anterior chamber VK of the eye 2 is determined on the basis of the determined eye structures by a functional supplementary module in the external planning device 4, in particular on the basis of (three-dimensional) reference structures 200 arranged in ring-shaped fashion about the center axis v, as described below in conjunction with step S7 for aligning a treatment model, and said center axis is used as a vertical reference axis of the planning device 4 or aligned with respect to the vertical reference axis of the planning device 4.

Figure 4:
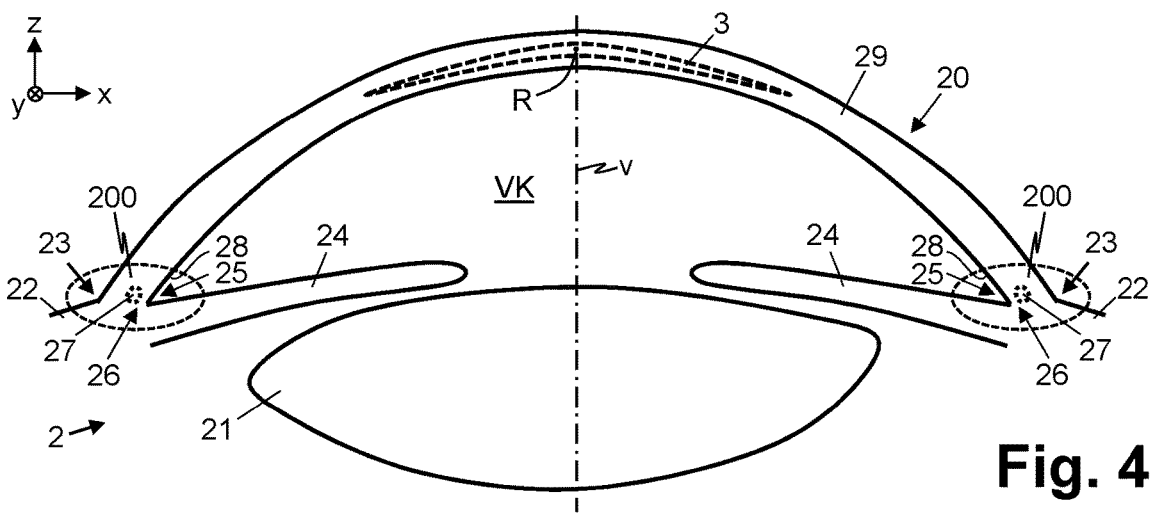
FIG. 4 schematically shows a cross section of an eye with eye structures, which are arranged in substantially ring-shaped fashion about a center axis of the anterior chamber of the eye, and a three-dimensional treatment pattern to be processed in the eye.

FIG. 4 schematically illustrates a cross section of the eye 2 to be treated and the three-dimensional treatment pattern 3 to be processed in the eye 2. In addition to the sclera 22, the cornea 29 and the lens 21 of the eye which define the extent of the anterior chamber VK of the eye 2, which is also referred to as anterior chamber of eye or "camera anterior bulbi", are visible in FIG. 4. Moreover, the center axis v of the anterior chamber VK is illustrated in FIG. 4. Depending on the definition, the anterior chamber VK of the eye 2 extends at least from the back surface 29p of the cornea 29 to the iris 24. In the present context, the region to the lens 21 of the eye is also considered to be part of the anterior chamber VK.

Figure 6:
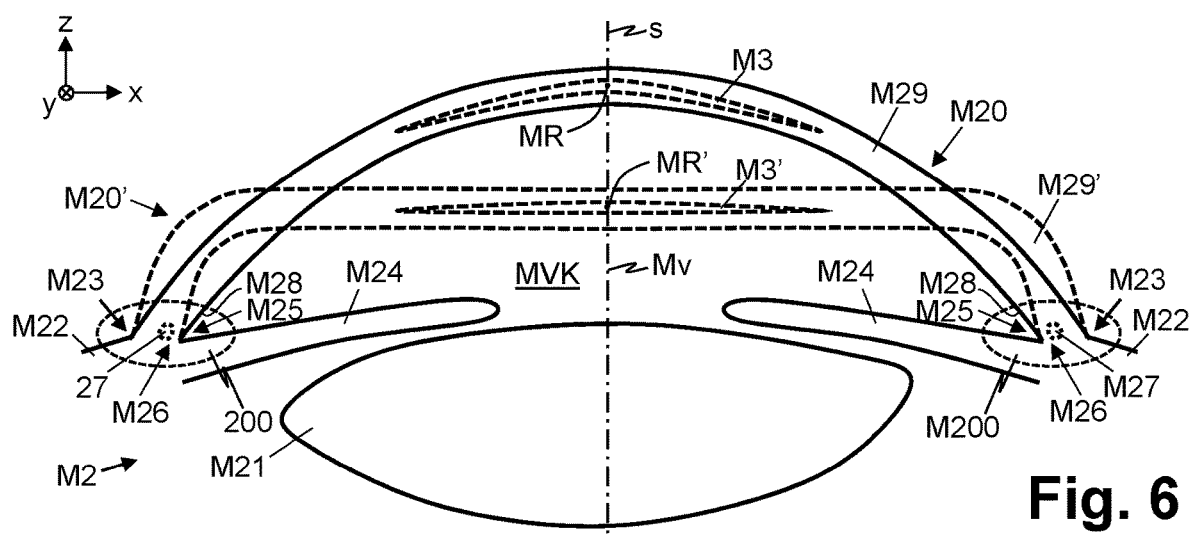
FIG. 6 schematically shows a cross section of a model of the eye in the deformed and non-deformed state, with the eye structures arranged in ring-shaped fashion about the center axis of the anterior chamber and a three-dimensional treatment model of the three-dimensional treatment pattern to be processed in the eye.

FIG. 6 schematically illustrates a cross section of an eye model M2 of the eye 2 illustrated in FIG. 4. The sclera 22, the cornea 29, the lens 21 of the eye and the anterior chamber VK of the eye 2, defined thereby, are reproduced in the eye model M2 as modeled eye structures of the sclera M22, cornea M29, lens M21 of the eye and anterior chamber MVK. In the eye model M2 of FIG. 6, the center axis v of the anterior chamber VK is denoted by Mv.

Moreover, reference structures 200, which are arranged in substantially ring-shaped (and concentric) fashion about the center axis v of the anterior chamber VK, are illustrated in the schematic cross-sectional illustration of the eye 2 in FIG. 4. These ring-shaped reference structures 200 of the anterior chamber VK or around the anterior chamber VK are of particular importance to the present ophthalmic device 1 and the method carried out therewith under the control of the circuit 10. These reference structures 200 include the limbus 23, the iris 24, the anterior chamber angle 25, the scleral spur 26, Schlemm's canal 27 and/or Schwalbe's line 28. In the eye model M2 of FIG. 6, the corresponding modeled reference structures are provided in the modeled structure of the anterior chamber MVK with the reference sign M200 and include the modeled eye structures of the limbus M23, iris M24, anterior chamber angle M25, scleral spur M26, Schlemm's canal M27 and/or Schwalbe's line M28.

Figure 5:
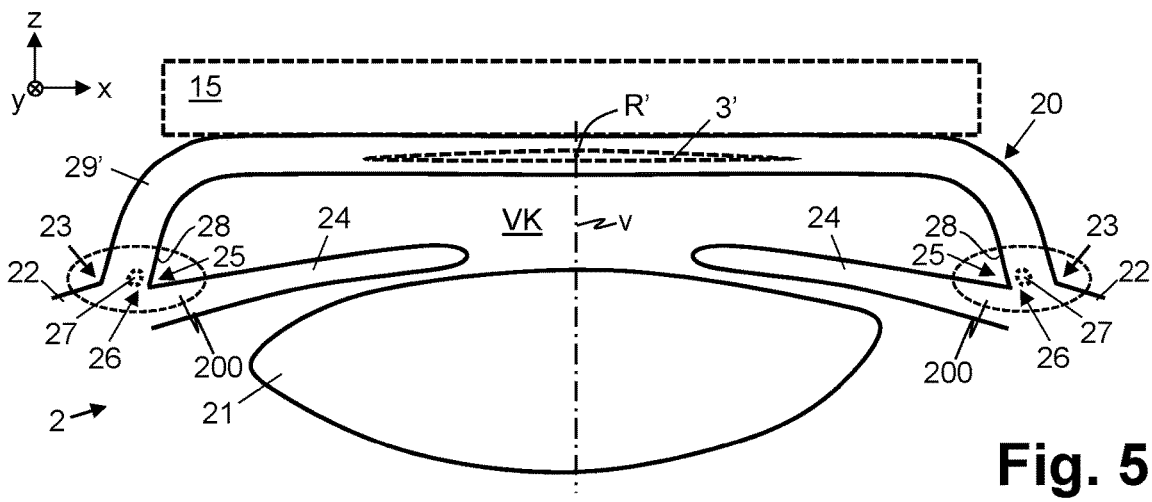
FIG. 5 schematically shows a cross section of the eye when it has been deformed by a contact body, with the eye structures arranged in ring-shaped fashion about the center axis of the anterior chamber and the three-dimensional treatment pattern to be processed in the eye.

FIG. 5 schematically illustrates a cross section of the eye 2 to be treated when it is docked to the application head 14 by means of the patient interface 13, within the scope of which the eye 2 is deformed by an applied contact body 15 of the patient interface 13. As is evident from the schematic illustration, it is predominantly the cornea 29 that is deformed in the process, whereas the reference structures 200 arranged in ring-shaped fashion about the center axis v of the anterior chamber VK remain substantially unchanged. Expressed differently the limbus 23, the iris 24, the anterior chamber angle 25, the scleral spur 26, Schlemm's canal 27 and Schwalbe's line 28 are not substantially deformed by the applied contact body 15.

Figure 13:
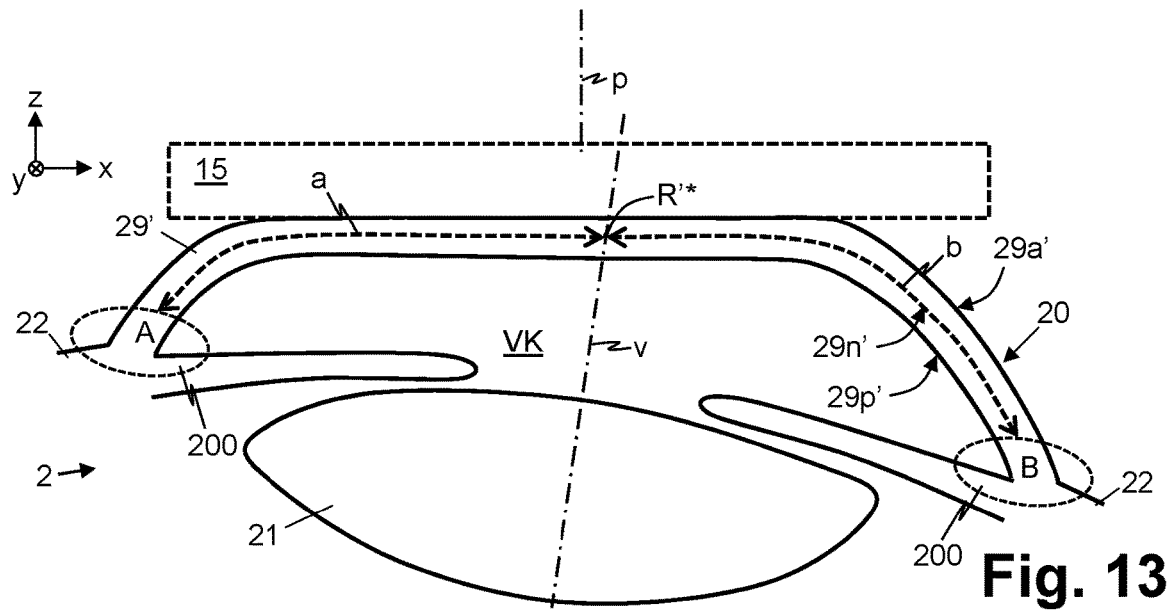
FIG. 13 schematically shows a cross section of the eye in the deformed state and with the alignment that has been tilted with respect to the optical axis of a focusing optic and a positioning reference point that has been displaced by the deformation and tilt and that is defined by distance specifications with respect to the eye structures arranged in ring-shaped fashion about the center axis of the anterior chamber.
Figure 14:
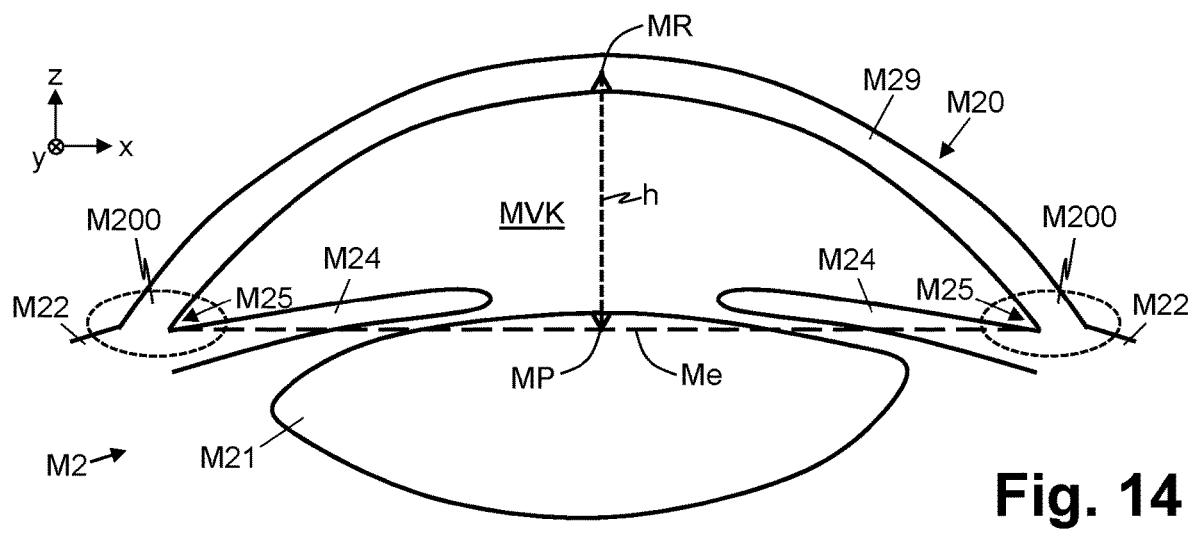
FIG. 14 schematically shows a cross section of the eye model with a positioning reference point for positioning the three-dimensional treatment model, said positioning reference point being defined with respect to a reference plane that extends through eye structures arranged in ring-shaped fashion about the center axis of the anterior chamber.
Figure 16:
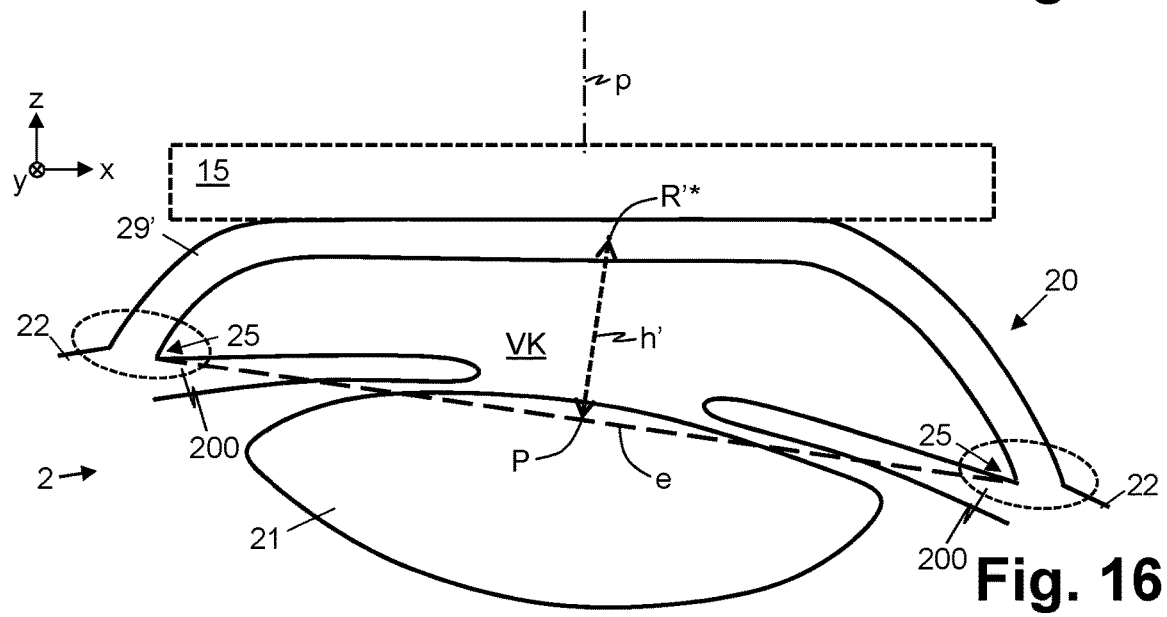
FIG. 16 schematically shows a cross section of the eye in the deformed state and with the alignment that has been tilted with respect to the optical axis of a focusing optic and a positioning reference point that has been displaced by the deformation and tilt and that is defined with respect to the reference plane that extends through the eye structures arranged in ring-shaped fashion about the center axis of the anterior chamber.
Figure 18:
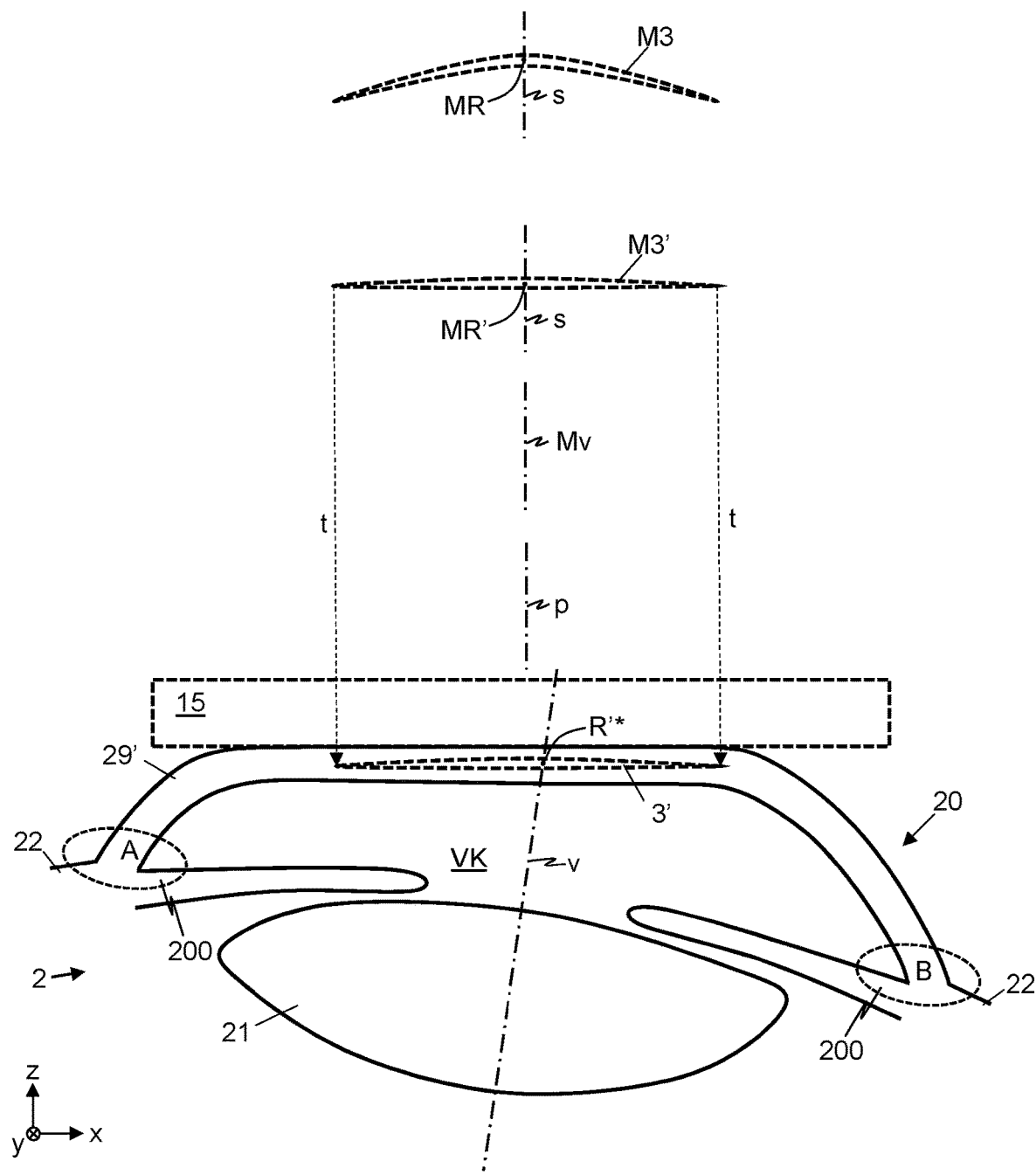
FIG. 18 schematically shows a cross section of the eye in the deformed state and with the alignment tilted with respect to the optical axis of a focusing optic and a three-dimensional treatment pattern to be processed in the eye in accordance with a three-dimensional treatment model, which is aligned with respect to the reference structures and positioned with respect to the positioning reference point that has been displaced by the deformation and tilt.

In the schematically illustrated cross section of the eye model M2 of FIG. 6, the model of the deformed eye 2 illustrated in FIG. 5 is also depicted; here, the modeled deformed eye tissue M20' or the model of the deformed cornea M29' is illustrated. Depending on the embodiment, the docking procedure of the application head 14 on the eye 2 to be treated by means of its patient interface 13 is modeled and an eye model M2 in the docked state is generated in optional step S10. Where necessary, the contact body 15 and the deformation caused by the application thereof on the eye 2 is modeled by a functional supplementary module in the external planning device 4 and the eye model M2 of the deformed eye 2, in particular the model of the deformed cornea M29', is generated on the basis of the non-deformed three-dimensional eye model M2. In an embodiment, respectively different variants of the eye model M2 of the deformed and tilted eye 2, in particular of the deformed and tilted cornea M29', are generated and stored for different degrees of tilt of the eye 2, for example in respect of the center axis v of its anterior chamber VK with respect to an optical axis p of the focusing optic 12, as illustrated in FIGS. 13, 16 and 18. Here, the functional supplementary module is a programmed software module which controls a processor of the external planning device 4 (or of the circuit 10) in such a way that the latter carries out the specified supplementary functions in the external planning device 4 (or in the circuit 10).

In step S2, the three-dimensional treatment model M3 of the three-dimensional treatment pattern 3 to be processed in the eye 2 is defined and stored on the basis of the generated (deformed or non-deformed) eye model M2. This is carried out by a user by means of suitable software applications in the external planning device 4, e.g., in the eye model M2 by means of computer-assisted design programs (CAD applications), which are known to a person skilled in the art, and this is determined by the desired treatment of the eye 2, for example a certain refractive correction of the eye 2 or any other treatment intervention by means of the pulsed laser beam L in the eye tissue 20 or on an object (implant) arranged in the eye 2.

In the example of FIG. 4, the three-dimensional treatment pattern 3 to be processed in the eye 2 is illustrated schematically as a three-dimensional treatment pattern in the cross section using a dashed line, e.g., an incision pattern for a three-dimensional tissue volume such as a lenticule or any other form that should be cut in the cornea 29. Moreover, a positioning reference point R of the treatment pattern 3 to be processed in the eye 2 is illustrated in FIG. 4, said positioning reference point R being explained in more detail below in conjunction with the three-dimensional treatment model M3 of the treatment pattern 3 to be processed. In the eye model M2 of FIG. 6, the corresponding three-dimensional treatment model M3 is likewise reproduced within the modeled eye structure of the cornea M29 using a dashed line. As schematically illustrated in FIG. 6, the center axis s of the three-dimensional treatment model M3 extends parallel to the center axis Mv of the modeled anterior chamber MVK in the eye model M2.

FIG. 5 also schematically illustrates the three-dimensional treatment pattern 3', to be processed in the eye 2, in the correspondingly deformed state. In the eye model M2 of FIG. 6, the corresponding three-dimensional deformed treatment model M3' is likewise reproduced within the modeled eye structure of the deformed cornea M29' using a dashed line. Depending on the embodiment, the user defines the treatment model M3 of the treatment pattern 3, to be processed, in the non-deformed state of the eye 2 or the eye model M2 in the case of a planned use of the contact body 15 and the functional supplementary module of the external planning device 4 (or of the circuit 10) generates a deformed treatment model M3' in optional step S11, or the user defines the deformed treatment model M3' in the eye model M2 of the eye 2, in the deformed state in the model of the deformed eye tissue M20', in particular in the model of the deformed cornea M29'. Consequently, in optional step S11, the docking procedure of the application head 14 on the eye 2 to be treated by means of the patient interface 13 of said application head is modeled in respect of the influence thereof on the treatment model M3 and a treatment model M3' is generated in the docked state. In an embodiment, respectively different variants of the treatment model M3' in the docked state are generated and stored for various degrees of tilt of the eye 2, for example in respect of the center axis v of its anterior chamber VK with respect to the optical axis p of the focusing optic 12.

In step S3, positioning data for positioning the three-dimensional treatment model M3 (or the generated deformed treatment model M3') are determined and stored. This is implemented in automated fashion and/or in user-defined fashion by means of a programmed software module of a functional supplementary module, which is executed on a processor of the external planning device 4 or of any other computer. To this end, a positioning reference point MR for positioning the three-dimensional treatment model M3 (or a positioning reference point MR' for positioning the deformed treatment model M3') is initially defined in the eye 2 or in the eye model M2. By way of example, the positioning reference point MR (MR') is an automatically selected center point or "centroid" in the defined treatment model M3 (or in the deformed treatment model M3') or a selected point, defined by the user using a mouse pointer (cursor) and/or any other operating element, in the defined treatment model M3 (or in the deformed treatment model M3'). The positioning reference point MR for the defined treatment model M3 is illustrated in FIG. 6, for example. Moreover, FIG. 6 depicts a positioning reference point MR' for the deformed treatment model M3'. It should be pointed out here that the positioning reference point MR, MR' need not lie on the center axis v, Mv of the anterior chamber VK, MVK, as illustrated in the figures, but it may also be defined at different positions in the treatment model M3, M3' or in the eye model M2 by the user or by the functional supplementary module.

Next, reference measurement data m for subsequently positioning the positioning reference point MR, MR' with respect to the reference structures 200 in the eye 2 are determined for the defined positioning reference point MR, MR'. To this end, the reference measurement data m for the positioning reference point MR, MR' in the eye model M2 are determined with respect to the modeled reference structures M200 of the modeled anterior chamber MVK, in particular with respect to the modeled eye structures of the limbus M23, iris M24, anterior chamber angle M25, scleral spur M26, Schlemm's canal M27 and/or Schwalbe's line M28.

Figure 19:
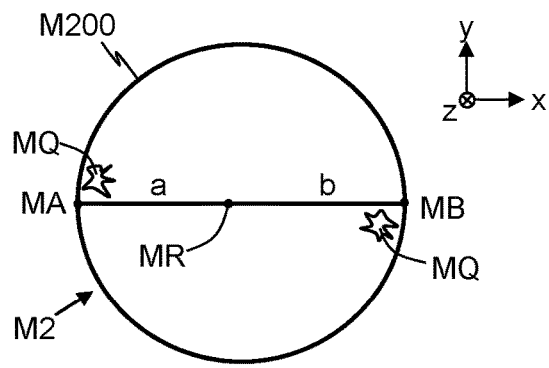
FIG. 19 schematically shows a plan view of the eye model with the eye structures arranged in ring-shaped fashion about the center axis of the anterior chamber, with two opposing points and distances of a positioning reference point in this respect.
Figure 21:
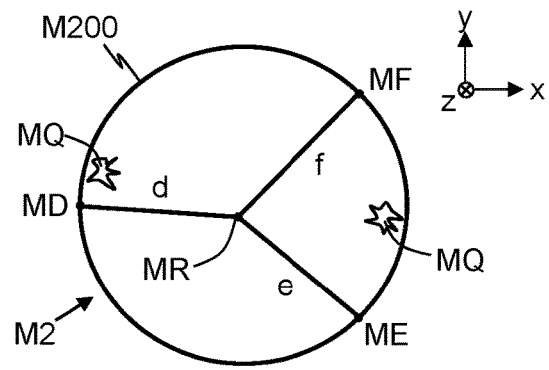
FIG. 21 schematically shows a plan view of the eye model with the eye structures arranged in ring-shaped fashion about the center axis of the anterior chamber, with three points located thereon and distances of a positioning reference point in this respect.
Figure 23:
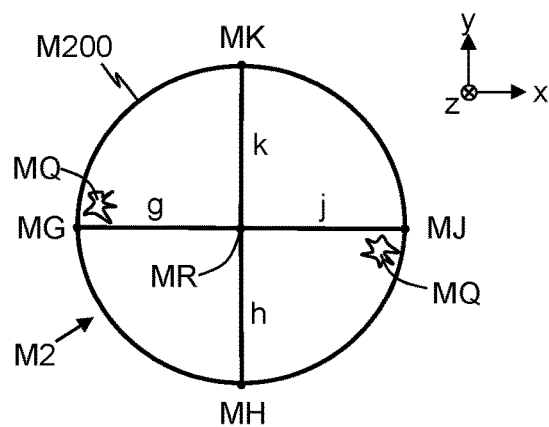
FIG. 23 schematically shows a plan view of the eye model with the eye structures arranged in ring-shaped fashion about the center axis of the anterior chamber, with four points located thereon and distances of a positioning reference point in this respect.

In a first embodiment, m distance specifications from the positioning reference point MR, MR' in the eye model M2 in relation to selected reference points on the modeled reference structures M200 of the modeled anterior chamber MVK are used as reference measurement data. As is evident in the plan view of the eye model M2 in FIG. 19, reference points MA, MB are selected in the eye model M2, said reference points lying opposite one another on the modeled ring-shaped reference structures M200, and the distances a, b from the positioning reference point MR, MR' in the eye model M2 to these reference points are captured (determined and stored) as reference measurement data m. By way of example, the relative position of the reference points MA, MB on the ring-shaped reference structures M200 in the eye model M2 is defined in this case by means of polar coordinates with respect to the center axis Mv of the anterior chamber MKV using structural and/or geometrically determinable features or patterns MQ in the eye tissue 20 for determining the rotation about the center axis Mv of the anterior chamber MKV, for example features and/or patterns of the iris M24 from a plan-view image of the eye 2. In alternative embodiments of FIGS. 21 and 23, a plurality of distributed (e.g., in thirds or quarters) reference points MD, ME, MF, MG, MH, MJ, MK are chosen on the modeled ring-shaped reference structures M200 in the eye model M2 and the distances d, e, f, g, h, j and k from the positioning reference point MR, MR' in the eye model M2 to these reference points MD, ME, MF, MG, MH, MJ, MK are captured as reference measurement data m. Consequently, the reference points MA, MB, MC, MD, ME, MF, MG, MEI, MJ, MK are located correspondingly on the modeled eye structures of the limbus M23, iris M24, anterior chamber angle M25, scleral spur M26, Schlemm's canal M27 and/or Schwalbe's line M28.

Figure 7:
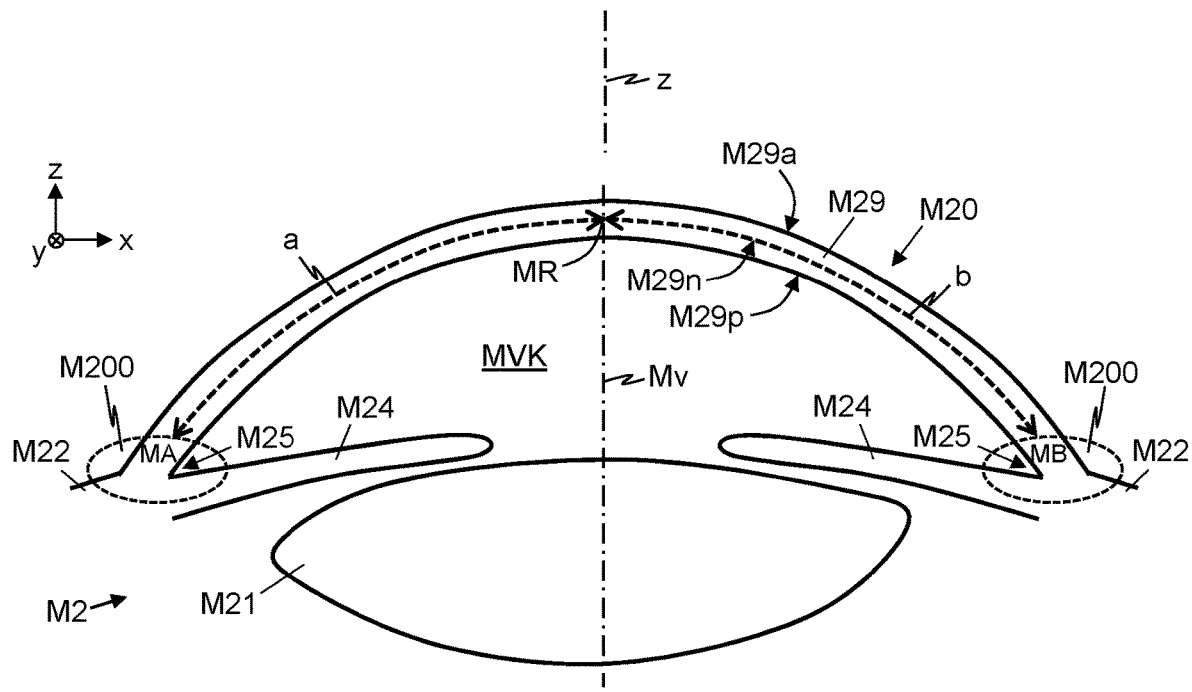
FIG. 7 schematically shows a cross section of the eye model with a positioning reference point for positioning the three-dimensional treatment model, said positioning reference point being defined by means of distance specifications with respect to the eye structures arranged in ring-shaped fashion about the center axis of the anterior chamber.
Figure 11:
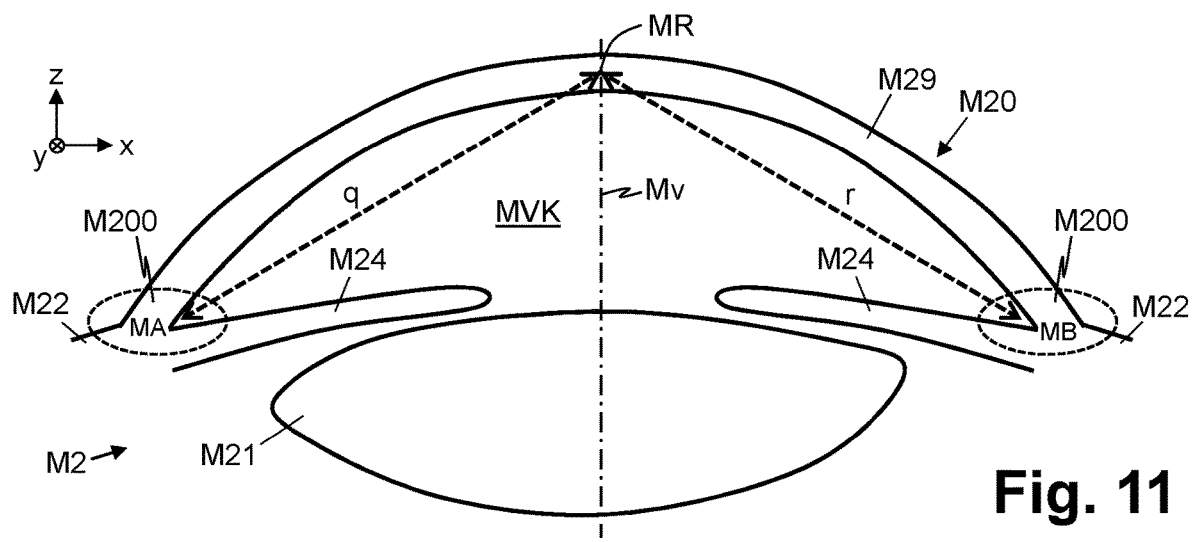
FIG. 11 schematically shows a cross section of the eye model with a positioning reference point for positioning the three-dimensional treatment model, said positioning reference point being defined by means of distances with respect to eye structures arranged in ring-shaped fashion about the center axis of the anterior chamber.

In FIG. 7, the distances a, b of the positioning reference point MR are illustrated schematically with respect to the two opposing reference points MA, MB on the modeled ring-shaped reference structures M200 in the cross section of the eye model M2. Even though this is not described or depicted in any more detail here, the explanations also apply accordingly to a plurality of reference points MA, MB, MC, MD, ME, MF, MG, MH, MJ, MK. According to the embodiment in FIG. 7, the distances a, b correspond to paths that extend along modeled eye structures of the eye model M2. In the example of FIG. 7, the distances a, b correspond to paths that extend along a neutral axis M29n in the cornea M29 (the neutral axis of the cornea is particularly advantageous because its length does not change, even in the case of a deformation of the cornea by way of an applied contact body 15). In further embodiments, the distances a, b correspond to paths that extend along the modeled outer (front) surface of the cornea 29a or along the modeled inner (back) surface of the cornea 29p. In a further embodiment, the distances q, r are determined as direct, shortest paths between the positioning reference point MR and the reference points MA, MB on the modeled ring-shaped reference structures M200, as illustrated in the example of FIG. 11.

Figure 12:
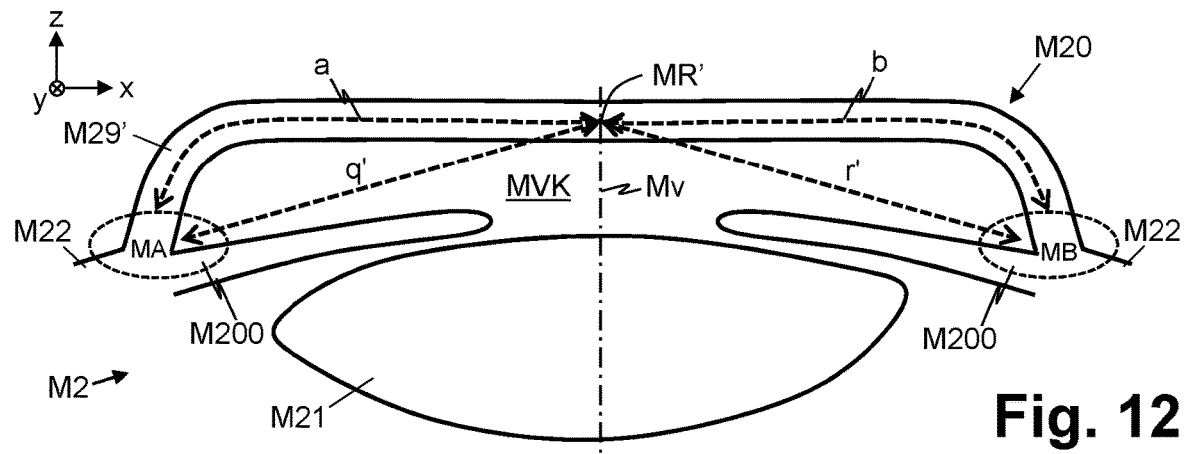
FIG. 12 schematically shows a cross section of the eye model in a deformed state and a positioning reference point that has been displaced by the deformation, said positioning reference point being defined by means of shortened distances with respect to the eye structures arranged in ring-shaped fashion about the center axis of the anterior chamber.

In FIG. 12, the first embodiment applied to the eye model M2 in the deformed state of the eye 2 is illustrated schematically in a cross section. In FIG. 12, the paths a, b of the positioning reference point MR' (along the neutral axis 29n of the cornea 29) in the eye model M2 of the deformed state of the eye 2 are illustrated schematically with respect to two opposing reference points MA, MB on the modeled ring-shaped reference structures M200. Moreover (alternatively), FIG. 12 illustrates the direct distances q', r' of the positioning reference point MR' in the eye model M2 of the deformed state of the eye 2 schematically with respect to the two opposing reference points MA, MB. It should be pointed out here that the ratio q:r of the direct distances q, r in the eye model M2 of FIG. 11 to a first approximation corresponds to the ratio q':r' of the direct distances q', r' in the eye model M2 of the deformed state of the eye 2 of FIG. 12. The smaller the deformation, the better the approximation. Hence, the use of the neutral axis 29n is particularly advantageous since there is no deformation present in that case. In fact, the paths a, b along the neutral axis 29n of the cornea 29 in the eye model M2 of FIG. 7 correspond to the paths a, b along the neutral axis 29n of the cornea 29 in the eye model M2 of the deformed state of the eye 2 of FIG. 12. Furthermore, the (outer) front face 29a and the (inner) back face 29p of the cornea 29 are advantageous since, firstly, they can be measured very well and, secondly, the strain thereof along the surfaces is very low on account of the rigidity of the cornea 29. The ratio remains the same, independently of the deformation. The distances q', r', which have been shortened by the deformation, are either determined in the deformed eye model M2 or, should the deformation be known or available from calculation, calculated on the basis of the deformation caused by the contact body 15 from the distances q, r determined in the eye model M2 of the eye 2 in the non-deformed state. Here, too, the explanations apply accordingly, as mentioned above, to a plurality of reference points MA, MB, MC, MD, ME, MF, MG, MH, MJ, MK.

Figure 9:
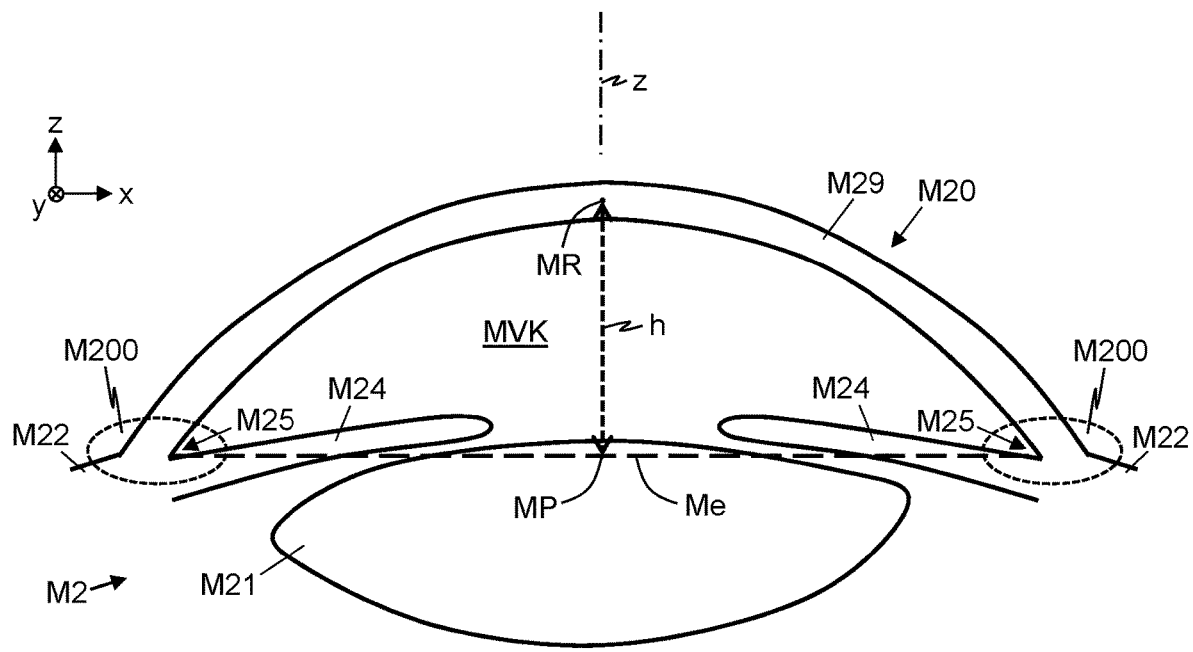
FIG. 9 schematically shows a cross section of the eye model with a positioning reference point for positioning the three-dimensional treatment model, said positioning reference point being defined with respect to a reference plane that extends through eye structures arranged in ring-shaped fashion about the center axis of the anterior chamber.

FIG. 9 depicts a second embodiment for capturing reference measurement data m, in which a reference plane Me is determined, which is defined by the modeled ring-shaped reference structures M200 of the modeled anterior chamber MVK. By way of example, the reference plane Me extends through the modeled eye structures of the limbus M23, iris M24, anterior chamber angle M25, scleral spur M26, Schlemm's canal M27 or Schwalbe's line M28. A distance specification h and a projection point MP of the positioning reference point MR with respect to the reference plane Me are determined and stored as reference measurement data m (a normal on the reference plane Me through the projection point Mp extends through the positioning reference point MR). The projection point MP of the positioning reference point MR on the reference plane Me is set during the planning with respect to structural and/or geometrically determinable features or patterns MQ, for example as a center point of a plurality of reference structures on the reference plane Me. Then, the positioning reference point MR is determined in the three-dimensional treatment model M3 on the normal extending through the set projection point MP on the reference plane Me and defined by means of the distance specification h to the projection point MP. A person skilled in the art will appreciate that, within the scope of an alternative variant, the positioning reference point MR can be defined at a distance from this normal by means of an additional offset value. By way of example, the projection point MP is defined by means of polar coordinates with respect to the center axis Mv of the anterior chamber MKV using structural and/or geometrically determinable features or patterns MQ in the eye tissue 20 for determining the rotation about the center axis Mv of the anterior chamber MKV, for example features and/or patterns of the iris M24 from a plan-view image of the eye 2, as was described above for the reference points on the ring-shaped reference structures M200.

Figure 15:
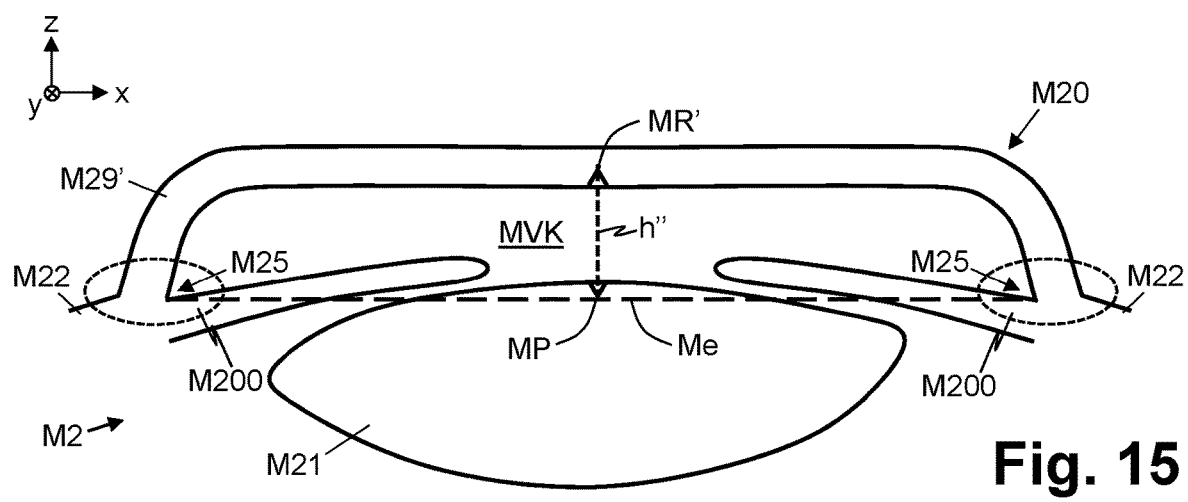
FIG. 15 schematically shows a cross section of the eye model in a deformed state and a positioning reference point that has been displaced by the deformation and that is defined with respect to the reference plane that extends through the eye structures arranged in ring-shaped fashion about the center axis of the anterior chamber.

In FIG. 15, the second embodiment applied to the eye model M2 in the deformed state of the eye 2 is illustrated schematically in a cross section. The distance h", which has been shortened by the deformation, is either determined in the deformed eye model M2 or calculated on the basis of the deformation caused by the contact body 15 from the distance specification h determined in the eye model M2 of the eye 2 in the non-deformed state. It should be noted here that the shortened distance h', h" not only depends on the degree of the deformation but also has different values for different variants of the eye model M2 for the deformed and tilted eye 2 with different degrees of tilt of the eye 2.

In step S4, the application head 14 is placed on the eye 2 to be treated and affixed to the eye 2 by means of the patient interface 13.

In step S5, (e.g., three-dimensional) eye structures of the eye 2 are optically captured and stored in digitized fashion when the application head 14 or the patient interface 13 is docked on and affixed to the eye 2 to be treated. This is carried out by means of the measurement system 16, controlled by the circuit 10. For a better understanding, the term "in-situ eye model" is used below for the captured (possibly three-dimensional) eye structures of the eye 2 to be treated when the application head 14 or the patient interface 13 is docked on and affixed to the eye 2 to be treated, in contrast to the eye model M2, which is determined and stored by means of the planning device 4 prior to the treatment. It should be noted here that the in-situ eye model captured by means of the measurement system 16 and the associated eye structures in an embodiment are captured as a three-dimensional eye model or as three-dimensional eye structures, even if the figures only illustrate two-dimensional cross-sectional images in each case and the following explanations do not explicitly refer to a three-dimensional in-situ eye model or three-dimensional eye structures.

Figure 8:
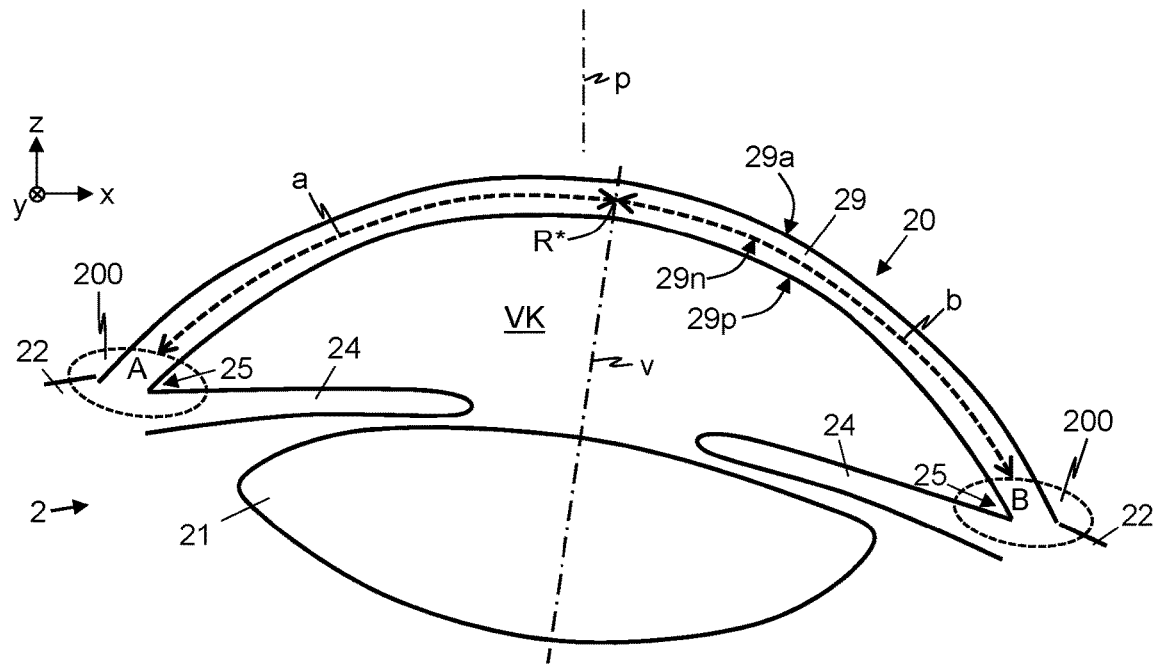
FIG. 8 schematically shows a cross section of the eye with an alignment that has been tilted with respect to an optical axis of a focusing optic and a positioning reference point that has been displaced by the tilt and that is defined by the distance specifications with respect to the eye structures arranged in ring-shaped fashion about the center axis of the anterior chamber.
Figure 10:
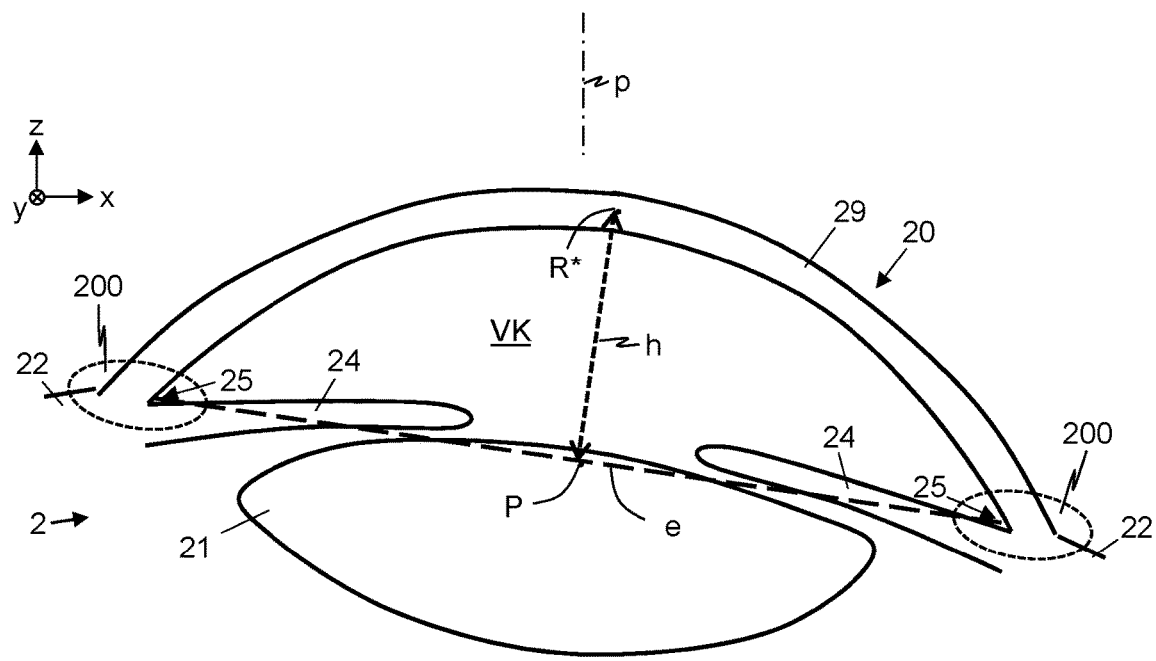
FIG. 10 schematically shows a cross section of the eye with the alignment that has been tilted with respect to the optical axis of a focusing optic and a positioning reference point that has been displaced by the tilt and that is defined with respect to the reference plane that extends through the eye structures arranged in ring-shaped fashion about the center axis of the anterior chamber.
Figure 17:
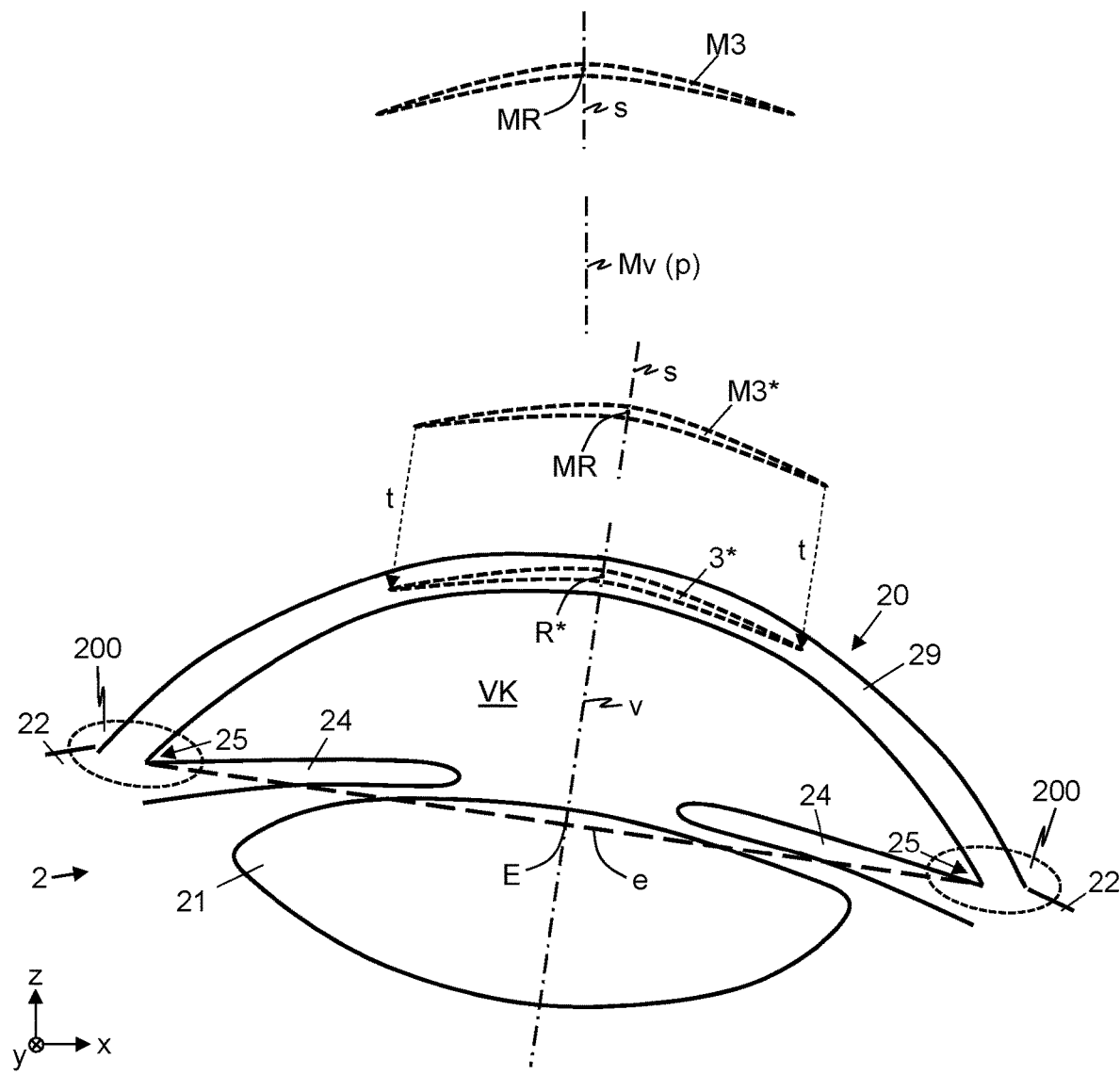
FIG. 17 schematically shows a cross section of the eye with the alignment tilted with respect to the optical axis of a focusing optic and a three-dimensional treatment pattern to be processed in the eye in accordance with a three-dimensional treatment model, which is aligned with respect to the reference structures and positioned with respect to the positioning reference point that has been displaced by the tilt.

FIGS. 8, 10, 13, 16, 17 and 18 schematically depict a cross section of the eye 2 or the in-situ eye model and the optically captured eye structures when the application head 14 is docked, wherein the eye 2, as illustrated in FIG. 2, has a tilted alignment with respect to the optical axis p of the focusing optic 12; i.e., the center axis v of the anterior chamber VK extends neither coaxially nor parallel with respect to the optical axis p of the focusing optic 12. Here, FIGS. 8, 10 and 17 depict the eye 2 or the corresponding in-situ eye model in the docked state without the application of a contact body 15 and consequently without a deformation. FIGS. 13, 16 and 18 depict the eye 2 or the corresponding in-situ eye model in the docked state with the application of a contact body 15 and with a deformation of the eye tissue 20, in particular of the cornea 29', caused thereby. As is evident in FIG. 8, the optically captured eye structures of the eye 2 or the in-situ eye model include the cornea 29 with its outer (front) corneal surface 29a and its inner (back) corneal surface 29p, the iris 24 and the lens 21 of the eye, which define the anterior chamber VK, and further eye structures in the region of the transition, framed by dashed lines, from the cornea 29 to the sclera 22 at the outer (front) surface of the cornea 29a, and the anterior chamber angle 25 at the inner (back) surface of the cornea 29p, which are determined and used as reference structures 200, as will be explained below.

In step S6, the circuit 10 determines reference structures 200 of the eye 2, which are arranged in substantially ring-shaped fashion about the center axis v of the anterior chamber VK, on the basis of the optically captured eye structures of the eye 2 or of the in-situ eye model, which are stored in digitized form. The ring-shaped arrangement about the center axis v of the anterior chamber VK is evident in the plan view in FIGS. 20, 22 and 24, wherein, on account of its significance, it is noted here that this plan view applies to the eye 2 both in the non-deformed state (see FIG. 4) and in the docked, deformed state (see FIG. 5) since the ring-shaped reference structures 200 remain substantially unchanged by the deformation during docking (the same applies accordingly to the plan view of FIGS. 19, 21 and 23 and the eye model M2 illustrated in FIG. 6 in the non-deformed and deformed state). The ring-shaped reference structures 200 include the limbus 23, the iris 24, the anterior chamber angle 25, the scleral spur 26, Schlemm's canal 27 and/or Schwalbe's line 28, which were mentioned above with reference to FIG. 4 and also reproduced in detail in FIGS. 5 and 6 (in FIGS. 7-18 and 25-26, the same ring-shaped reference structures 200 are only depicted for reasons of simplicity in summarized fashion by way of the region indicated by dashed lines and provided with the reference sign 200).

In step S7, the circuit 10 defines the alignment of the defined three-dimensional treatment model M3 for treating the eye 2 that has been tilted with respect to the optical axis p of the focusing optic 12, i.e., for processing the treatment pattern 3, 3', determined by the treatment model M3 or the deformed treatment model M3', in the eye tissue 20. It should be noted here that the alignment of the three-dimensional treatment model M3 need not be determined if the treatment model M3 is aligned for a treatment pattern 3 in the cornea 29 and the cornea 29 is shaped into a defined relative position by means of the contact body 15 of the patient interface 13, as illustrated in FIGS. 13, 16 and 18, where the eye 2 or the corresponding in-situ eye model is illustrated in the docked state and the eye tissue 20, in particular the cornea 29', is deformed by the contact body 15 and comprises a defined relative position with respect to the optical axis p of the focusing optic 12. Otherwise the three-dimensional treatment model M3 is aligned with respect to the reference structures 200, determined in the docked state of the application head 14, in the in-situ eye model. Here, the three-dimensional treatment model M3 is aligned with respect to the reference structures 200, determined in the docked state of the application head 14, of the eye or of the in-situ eye model, proceeding from a coaxial or parallel alignment of the center axis s of said treatment model with respect to the center axis Mv of the anterior chamber MVK in the eye model M2. For the purposes of aligning the three-dimensional treatment model M3 or its center axis s, the circuit 10 determines a reference plane e extending through the reference structures 200 and/or the center axis v of the anterior chamber VK of the eye 2 or of the in-situ eye model, which extends normally with respect to the reference plane e through a center point E of the determined ring-shaped reference structures 200 of the in-situ eye model (see FIGS. 17 and 18). For the purposes of treating the eye 2 in the docked, tilted state, the circuit 10 aligns the three-dimensional treatment model M3, proceeding from its initial alignment, in such a way that the central axis s in the three-dimensional treatment model M3 extends normally with respect to the reference plane e or parallel to the center axis v of the anterior chamber VK. For illustrative purposes, the defined three-dimensional treatment model M3 is illustrated schematically with its center axis s in FIG. 17, said center axis being aligned parallel to the center axis Mv of the anterior chamber MKV in the eye model M2 and hence parallel to the optical axis p of the non-tilted focusing optic 12. The three-dimensional treatment model M3*, which is aligned with respect to the reference plane e or the center axis v of the anterior chamber VK in the tilted eye 2 or in the in-situ eye model, is likewise illustrated schematically in FIG. 17. Reference sign 3* relates to the treatment pattern to be processed in the eye 2, which treatment pattern is defined by the tilted three-dimensional treatment model M3* that is aligned with respect to the reference plane e or the center axis v of the anterior chamber VK of the eye 2, when it is positioned at the envisaged, planned position R* in the eye 2, as explained below. FIG. 18 schematically illustrates the deformed three-dimensional treatment model M3' with its center axis s. Reference sign 3' relates to the deformed treatment pattern to be processed in the eye 2, which treatment pattern is defined by the deformed three-dimensional treatment model M3', when it is positioned at the envisaged, planned position R'* in the eye 2 or in the in-situ eye model, as explained below.

In step S8, the circuit 10 determines the positioning of the possibly aligned and/or deformed three-dimensional treatment model M3*, M3'* for treating the eye 2 that has been tilted with respect to the optical axis p of the focusing optic 12. To this end, the circuit 10 uses the positioning reference point MR, MR' of the (possibly deformed) three-dimensional treatment model M3, M3' (M3*, M3'*), the position of which is defined by way of its reference measurement data m with respect to the reference structures M200 in the eye model M2, and determines a displaced (tilted) positioning reference point R*, R'* in the tilted eye 2 or in the in-situ eye model. The circuit 10 determines the displaced (tilted) positioning reference point R*, R'* using the reference measurement data m in respect of the determined reference structures 200 in the tilted eye 2 or in the in-situ eye model.

In optional step S12, the circuit 10 determines the influence on the treatment model M3 of the actual docking procedure of the application head 14, by means of its patient interface 13, on the eye 2 and generates a treatment model M3' for the actual docked state. If a treatment model M3' is already available for the docked state from the functional module of the planning device 4, the circuit 10 generates an adapted treatment model M3' for the actual docked state; otherwise, the circuit 10 generates the treatment model M3' for the actual docked state on the basis of the original treatment model M3 from the planning device 4. In the actually docked state of the application head 14 or of the patient interface 13 on the eye 2, the eye 2 is determined by the in-situ eye model, determined in this state and stored in step S5, with the captured eye structures of the eye 2. The treatment model M3' generated or adapted for the actual docked state emerges from the treatment model M3 or from the deformed treatment model M3' in accordance with the mapping of the eye model M2 or of the deformed eye model M2' onto the in-situ eye model of the eye 2 in the docked state. A person skilled in the art will appreciate that a constant volume of the eye 2 can be assumed during the deformation of the eye 2 by a contact body 15 during the docking on account of the rigidity and low elasticity of the cornea 29. Moreover, as already mentioned above, the ring-shaped reference structures 200 remain substantially unchanged during the deformation of the eye 2, and so the mapping of the eye model M2 or of the deformed eye model M2' onto the in-situ eye model of the eye 2 in the docked state is scalable on account of the dimensions of the ring-shaped reference structures 200 (in the originally captured eye model M2 and in the in-situ eye model of the eye 2 in the docked state). In an embodiment, the circuit 10 scales the eye model M2 or the deformed eye model M2' and the treatment model M3, positioned therein, of the treatment pattern 3 to be processed onto the size of the eye 2 in the docked (deformed) state as per the in-situ eye model on account of the ring-shaped reference structures M200, 200. Thereupon, the circuit 10 determines a mapping transformation for converting the eye model M2 or the deformed eye model M2' into the in-situ eye model of the eye 2 in the docked (deformed) state, for example on the basis of splitting the eye model M2 or the deformed eye model M2' and the in-situ eye model of the eye 2 in the docked (deformed) state into a finite number of corresponding elements (e.g., with the aid of the finite element method), wherein the mapping transformation transforms each element in the eye model M2 or in the deformed eye model M2' into a corresponding (transformed) element in the in-situ eye model of the eye 2 in the docked (deformed) state. The circuit 10 determines the treatment model M3' in the docked (deformed) state of the eye 2 from the treatment model in the scaled eye model M2 or in the scaled deformed eye model M2' on account of the corresponding transformed elements in the in-situ eye model of the eye 2 in the docked (deformed) state.

A person skilled in the art will appreciate that steps S7, for aligning the treatment model M3, and S8, for positioning the aligned treatment model M3*, can also be carried out in the reverse sequence such that the treatment model M3 is positioned first and the positioned treatment model is subsequently aligned with respect to the reference structures 200. As indicated in FIG. 3 by the dashed frame in step S7, an alignment of the treatment model M3 is not mandatory, as already explained above in conjunction with step S7.

Figure 20:
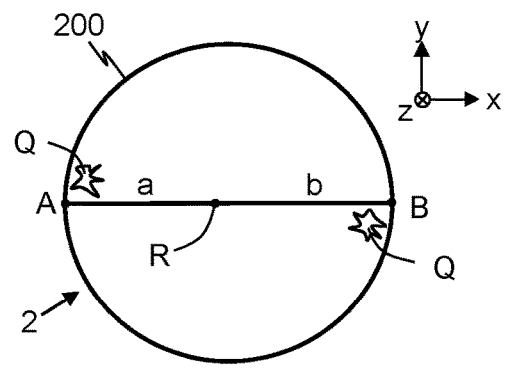
FIG. 20 schematically shows a plan view of the eye with the eye structures arranged in ring-shaped fashion about the center axis of the anterior chamber, with two opposing points and distances of a positioning reference point in this respect.
Figure 22:
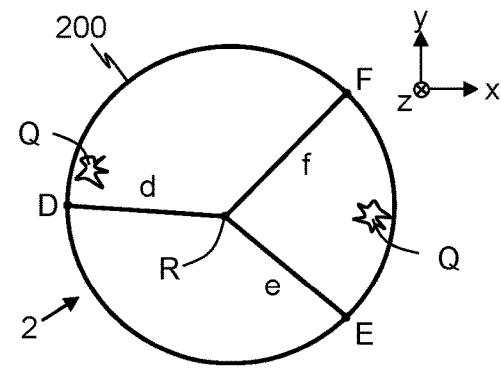
FIG. 22 schematically shows a plan view of the eye with the eye structures arranged in ring-shaped fashion about the center axis of the anterior chamber, with three points located thereon and distances of a positioning reference point in this respect.
Figure 24:
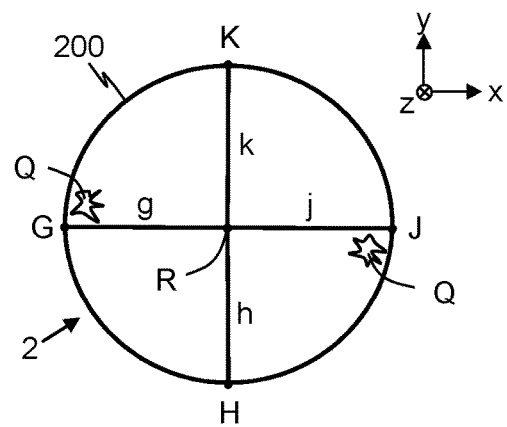
FIG. 24 schematically shows a plan view of the eye with the eye structures arranged in ring-shaped fashion about the center axis of the anterior chamber, with four points located thereon and distances of a positioning reference point in this respect.

According to the first embodiment, in which the reference measurement data m include distance specifications for determining the position of the positioning reference point MR, MR' in the eye model M2, the corresponding reference points A, B on the determined ring-shaped reference structures 200 of the tilted eye 2 are determined in the in-situ eye model on the basis of the reference points MA, MB captured in the eye model M2, for example using the structural and/or geometrically determinable features or patterns Q in the eye tissue 20 for determining the twist about the center axis v of the anterior chamber VK, as described above in relation to FIG. 19 and schematically depicted in FIG. 20. In the embodiments according to FIGS. 21 and 23 with a plurality of reference points MD, ME, MF, MG, MH, MJ, MK distributed in the eye model M2 (e.g., in sectors encompassing a third or a quarter), the corresponding reference points D, E, F, G, H, J, K on the determined ring-shaped reference structures 200 of the tilted eye 2 are determined in the in-situ eye model, as schematically depicted in FIGS. 20, 22 and 24.

As depicted schematically in the cross section in FIG. 8 and in a plan view in FIG. 20, the displaced (tilted) positioning reference point R* is determined in the in-situ eye model, proceeding from the determined reference points A, B, D, E, F, G, H, J, K on the determined ring-shaped reference structures 200 of the tilted eye 2, using the distances a, b, d, e, f, g, h, j, k, q, r to the positioning reference point MR stored for the eye model M2, in each case proceeding from the reference points A, B, D, E, F, G, H, J, K in the in-situ eye model as paths a, b, d, e, f, g, h, j, k along the corresponding eye structures in the in-situ eye model or, in the case of direct paths q, r, as points of intersection of spherical shells around the reference points A, B, D, E, F, G, H, J, K with the radius of the paths m, n. In the example of FIG. 8, the displaced (tilted) positioning reference point R* is determined proceeding from the determined reference points A, B in the in-situ eye model using the paths a, b, stored for the eye model M2, along the neutral axis 29n in the cornea 29 of the in-situ eye model.

FIG. 13 depicts the determination of the displaced (tilted) positioning reference point R'* in the deformed eye 2 using the example of the paths a, b, captured and stored for the eye model M2, proceeding from the determined reference points A, B on the ring-shaped reference structures 200 of the tilted eye 2 in the in-situ eye model. The paths a, b are guided along the neutral axis 29n' in the deformed cornea 29' in the in-situ eye model of the deformed eye 2. Depending on the accuracy when determining the neutral axis 29n' in the deformed cornea 29', or if the paths a, b in the eye model M2 are determined along the outer and/or inner corneal surfaces 29a, 29p and are transferred accordingly in the in-situ eye model to the outer and/or inner corneal surfaces 29p', 29a' of the deformed cornea 29', the displaced (tilted) positioning reference point R'* is determined by the unchanging ratio a:b of the paths. What also applies in this case, too, is that not only can use be made of the path lengths a, b to two opposing reference points on the ring-shaped reference structures 200 but that use can also be made of path lengths along eye structures to a plurality of reference points MA, MB, MC, MD, ME, MF, MG, MEI, MJ, MK and/or of direct distances q, r in this case.

According to the second embodiment, in which the reference measurement data m include a projection point MP of the positioning reference point MR on the reference plane Me defined by the ring-shaped reference structures M200 and a distance specification h from the positioning reference point MR to the reference plane Me or to the projection point MP, the corresponding projection point P is determined on the reference plane e defined in the in-situ eye model by the determined ring-shaped reference structures 200 of the tilted eye 2 on the basis of the projection point MP captured in the eye model M2, for example using the structural and/are geometrically determinable features or patterns Q in the eye tissue 20 for determining the twist about the center axis v of the anterior chamber VK, as explained above in conjunction with the determination of the reference points A, B, D, E, F, G, H, J, K.

As depicted schematically in the cross section of FIG. 10, the displaced (tilted) positioning reference point R* is determined proceeding from the determined projection point P on the reference plane e defined by the ring-shaped reference structures 200 of the tilted eye 2 in the in-situ eye model using the distance h, stored for the eye model M2, to the positioning reference point MR, as a distance point with the distance h on a normal to the reference plane e through the projection point P. FIG. 16 illustrates the same accordingly for the deformed eye 2, wherein the displaced (tilted) positioning reference point R'* is determined in the deformed eye tissue 20, in particular in the deformed cornea 29', in the in-situ eye model by means of the distance h' that has been shortened by the deformation.

As depicted in FIG. 17, the treatment model M3* aligned in step S7 is positioned at the displaced (tilted) positioning reference point R' for processing the treatment pattern 3* by way of the circuit 10; i.e., the positioning reference point MR of the aligned treatment model M3* is positioned at the determined positioning reference point R*, as depicted schematically by the dashed arrows t.

As depicted in FIG. 18, the treatment model M3' deformed in step S11 and/or S12 is positioned at the displaced (tilted) positioning reference point R'* for processing the treatment pattern 3' by way of the circuit 10; i.e., the positioning reference point MR' of the deformed treatment model M3' is positioned at the determined positioning reference point R'*, as depicted schematically by the dashed arrows t.

In step S9, when the application head 14 is affixed to the eye 2, the circuit 10 controls the laser source 11 and the scanner system 17 in such a way that the scanner system 17 directs, in accordance with the (deformed or non-deformed) three-dimensional treatment model M3*, M3' that is positioned with respect to the reference structures 200 and aligned when necessary, the pulsed laser beam L generated by the laser source 11 onto the treatment targets F of the three-dimensional treatment pattern 3*, 3' to be processed in the eye 2.

What is claimed is:

1. Ophthalmic device for treating an eye, comprising:
a laser source configured to generate a pulsed laser beam;
an application head with a focusing optic and a patient interface, wherein the focusing optic has an optical axis and is configured to focus the pulsed laser beam in the eye and wherein the patient interface is configured to affix the application head on the eye;
a circuit configured to store a three-dimensional treatment model of a three-dimensional treatment pattern to be processed in the eye and a reference point for positioning the three-dimensional treatment model in the eye;
a scanner system configured to direct the pulsed laser beam, in accordance with the three-dimensional treatment model, onto treatment targets of the three-dimensional treatment pattern to be processed in the eye; and
a measurement system configured to optically capture three-dimensional structures of the eye over a depth range extending in the direction of the optical axis of the focusing optic when the application head is affixed to the eye;
wherein the circuit is further configured:
to determine three-dimensional reference structures of the eye on the basis of the three-dimensional structures optically captured by the measurement system when the application head is affixed to the eye, which three-dimensional reference structures are arranged in essentially ring-shaped fashion about a center axis of the anterior chamber of the eye,
to determine, using the three-dimensional reference structures, a displaced reference point when the application head is affixed to the eye, and
to position the three-dimensional treatment model with respect to the displaced reference point when the application head is affixed to the eye, and
to control the scanner system to direct the pulsed laser beam, when the application head is affixed to the eye, in accordance with the three-dimensional treatment model positioned with respect to the displaced reference point, onto the treatment targets of the three-dimensional treatment pattern to be processed in the eye.

2. Ophthalmic device according to claim 1, wherein the circuit is configured:
to store the reference point with reference measurement data for positioning the reference point with respect to the three-dimensional reference structures when the application head is not affixed to the eye and
to determine the displaced reference point when the application head is affixed to the eye using the reference measurement data and the three-dimensional reference structures determined when the application head is affixed to the eye.

3. Ophthalmic device according to claim 2, wherein:
the reference measurement data include distance specifications from the reference point to at least two opposing points on the three-dimensional reference structures, when the application head is not affixed to the eye, and
the circuit is configured to determine the displaced reference point when the application head is affixed to the eye, using the distance specifications with respect to the at least two opposing points on the three-dimensional reference structures determined when the application head is affixed to the eye.

4. Ophthalmic device according to claim 3, wherein the distance specifications define path lengths along captured eye structures of the eye from the reference point to the at least two opposing points on the three-dimensional reference structures that are arranged in substantially ring-shaped fashion.

5. Ophthalmic device according to claim 4, wherein the distance specifications include path lengths along at least one of the following: neutral axis of the cornea, corneal front surface or corneal back surface.

6. Ophthalmic device according to claim 3, wherein the circuit is configured to determine the displaced reference point when the application head is affixed to the eye using a ratio of the distance specifications contained in the reference measurement data.

7. Ophthalmic device according to claim 2, wherein:
the reference measurement data include a distance specification and a projection point of the reference point with respect to a reference plane which is defined by three-dimensional reference structures captured when the application head is not affixed to the eye; and
the circuit is configured to determine the displaced reference point when the application head is affixed to the eye using the distance specification and the projection point of the reference point with respect to the reference plane when the application head is affixed to the eye, defined by the three-dimensional reference structures captured when the application head is affixed to the eye.

8. Ophthalmic device according to claim 1, wherein the circuit is configured:
to align the three-dimensional treatment model with respect to the three-dimensional reference structures and, when the application head is affixed to the eye,
to control the scanner system to direct the pulsed laser beam onto the treatment targets of the three-dimensional treatment pattern to be processed in the eye in accordance with the three-dimensional treatment model that has been aligned with respect to the three-dimensional reference structures.

9. Ophthalmic device according to claim 1, wherein the circuit is configured to determine, on the basis of the determined three-dimensional reference structures, a center axis of the anterior chamber defined by the three-dimensional reference structures and to align the three-dimensional treatment model with respect to the center axis of the anterior chamber.

10. Ophthalmic device according to claim 1, wherein the circuit is configured to determine a reference plane that extends through the three-dimensional reference structures and to align the three-dimensional treatment model with respect to the reference plane.

11. Ophthalmic device according to claim 1, wherein the three-dimensional reference structures include at least one of the following: limbus, iris, anterior chamber angle, scleral spur, Schlemm's canal or Schwalbe's line.

12. Ophthalmic device according to claim 1, wherein the circuit is configured to receive the three-dimensional treatment model via a communication path from an external planning device.

13. Ophthalmic device according to claim 1, wherein
the patient interface includes a contact body that rests on the eye when the application head is affixed to the eye and that deforms the eye; and
the circuit is configured:
to transform the three-dimensional treatment model into a deformed three-dimensional treatment model of a deformed three-dimensional treatment pattern to be processed in the eye,
to determine, using the three-dimensional reference structures, a displaced reference point when the application head is affixed to the eye and to position the deformed three-dimensional treatment model with respect to the displaced reference point when the application head is affixed to the deformed eye and,
to control the scanner system to direct the pulsed laser beam, when the application head is affixed to the deformed eye, in accordance with the deformed three-dimensional treatment model, positioned with respect to the displaced reference point, onto the treatment targets of the deformed three-dimensional treatment pattern to be processed in the eye.

14. Ophthalmic device for treating an eye, comprising:
a laser source configured to generate a pulsed laser beam;
an application head with a focusing optic and a patient interface, wherein the focusing optic has an optical axis and is configured to focus the pulsed laser beam in the eye and wherein the patient interface is configured to affix the application head on the eye;
a circuit which is configured to store a three-dimensional treatment model of a three-dimensional treatment pattern to be processed in the eye and a reference point for positioning the three-dimensional treatment model in the eye;
a scanner system which is configured to direct the pulsed laser beam, in accordance with the three-dimensional treatment model, onto treatment targets of the three-dimensional treatment pattern to be processed in the eye; and
an interferometric measurement system which is configured to optically capture three-dimensional structures of the eye over a depth range extending in the direction of the optical axis of the focusing optic when the application head is affixed to the eye;
wherein the circuit is further configured:
to determine reference structures of the eye on the basis of the three-dimensional structures optically captured by the interferometric measurement system when the application head is affixed to the eye, which reference structures are arranged in essentially ring-shaped fashion about a center axis of the anterior chamber of the eye,
to determine, using the reference structures, a displaced reference point when the application head is affixed to the eye, and
to position the three-dimensional treatment model with respect to the displaced reference point when the application head is affixed to the eye, and
to control the scanner system to direct the pulsed laser beam, when the application head is affixed to the eye, in accordance with the three-dimensional treatment model positioned with respect to the displaced reference point, onto the treatment targets of the three-dimensional treatment pattern to be processed in the eye.

* * * * *